US008668978B2

(12) United States Patent
Malima et al.

(10) Patent No.: US 8,668,978 B2
(45) Date of Patent: Mar. 11, 2014

(54) MULTI-BIOMARKER BIOSENSOR

(75) Inventors: Asanterabi Malima, Lynn, MA (US);
Ahmed Busnaina, Ashland, MA (US);
Salome Siavoshi, Cambridge, MA (US);
Sivasubramanian Somu, Boston, MA (US); Cihan Yilmaz, Boston, MA (US);
Tiziana Musacchio, Boston, MA (US);
Jaydev Upponi, Boston, MA (US);
Vladimir Torchilin, Charlestown, MA (US)

(73) Assignee: Northeastern University, Boston, MA (US)

(*) Notice: Subject to any disclaimer, the term of this patent is extended or adjusted under 35 U.S.C. 154(b) by 385 days.

(21) Appl. No.: 12/874,885

(22) Filed: Sep. 2, 2010

(65) Prior Publication Data

US 2011/0117582 A1 May 19, 2011

Related U.S. Application Data

(63) Continuation-in-part of application No. 12/085,883, filed as application No. PCT/US2006/045911 on Dec. 1, 2006.

(60) Provisional application No. 60/741,421, filed on Dec. 1, 2005, provisional application No. 61/239,145, filed on Sep. 2, 2009.

(51) Int. Cl.
*B32B 3/00* (2006.01)
*G01N 33/00* (2006.01)
*G01N 33/564* (2006.01)
*A61M 29/00* (2006.01)

(52) U.S. Cl.
USPC .......... 428/172; 428/167; 428/212; 435/7.92; 436/506; 436/517; 436/518; 436/543; 604/96.01; 606/191

(58) Field of Classification Search
USPC ................ 428/156, 172, 167, 212; 435/7.92; 436/501, 506, 517, 518, 543; 604/96.01; 606/191
See application file for complete search history.

(56) References Cited

U.S. PATENT DOCUMENTS

| 4,728,591 | A | * | 3/1988 | Clark et al. ...................... 430/5 |
|---|---|---|---|---|
| 4,969,468 | A | | 11/1990 | Byers et al. |
| 6,250,984 | B1 | | 6/2001 | Jin et al. |
| 6,630,772 | B1 | | 10/2003 | Bower et al. |
| 6,911,767 | B2 | | 6/2005 | Takai |
| 6,946,677 | B2 | | 9/2005 | Ostergard |
| 6,987,071 | B1 | | 1/2006 | Bollman et al. |
| 7,087,207 | B2 | | 8/2006 | Smalley et al. |
| 2001/0036745 | A1 | * | 11/2001 | Sandhu ...................... 438/736 |
| 2005/0029514 | A1 | | 2/2005 | Moriya |
| 2005/0100499 | A1 | | 5/2005 | Oya et al. |
| 2005/0202587 | A1 | | 9/2005 | Redecker et al. |

OTHER PUBLICATIONS

Yamamoto et al., "Orientation and purification of carbon nanotubes using ac electrophoresis", J. Phys. D: Appl. Phys. 31 No. 8 (L34-L36) 1998.
Yamamoto et al, "Orientation and purification of carbon nanotubes using ac electrophoresis": Jpn. J. Appll Phys. vol. 35 (L917-L918) 1996 (Abstract Only).

* cited by examiner

*Primary Examiner* — Donald J Loney
(74) *Attorney, Agent, or Firm* — McLane, Graf, Raulerson & Middleton, Professional Association

(57) ABSTRACT

Nanosubstrates as biosensors, methods of making such nanosubstrates, and methods of using such nanosubstrates to detect biomarkers are described.

27 Claims, 26 Drawing Sheets

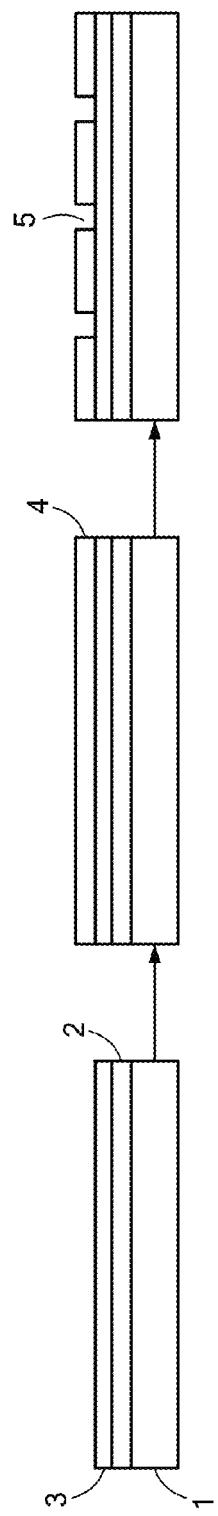
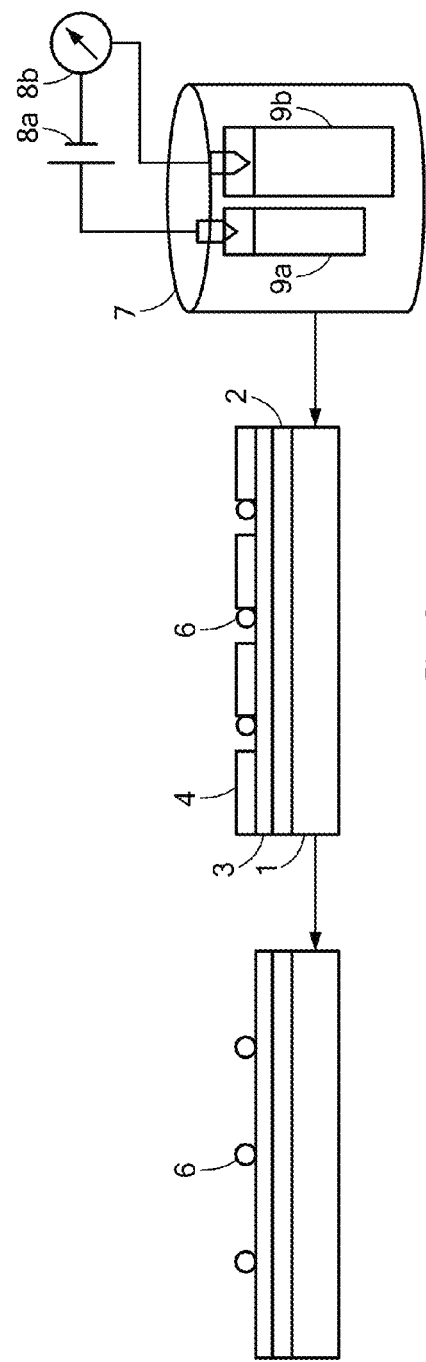

*FIG. 3B*
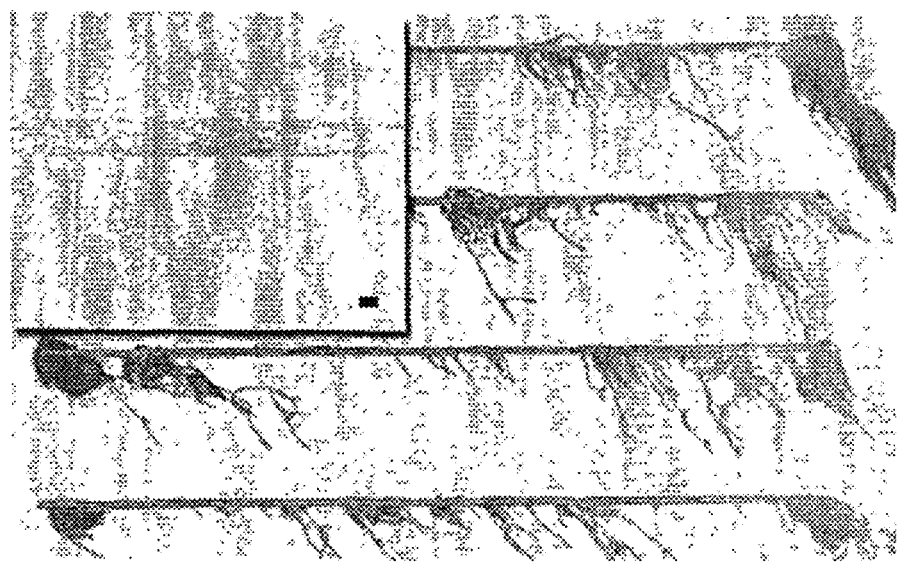
*FIG. 3A*
*FIG. 3D*
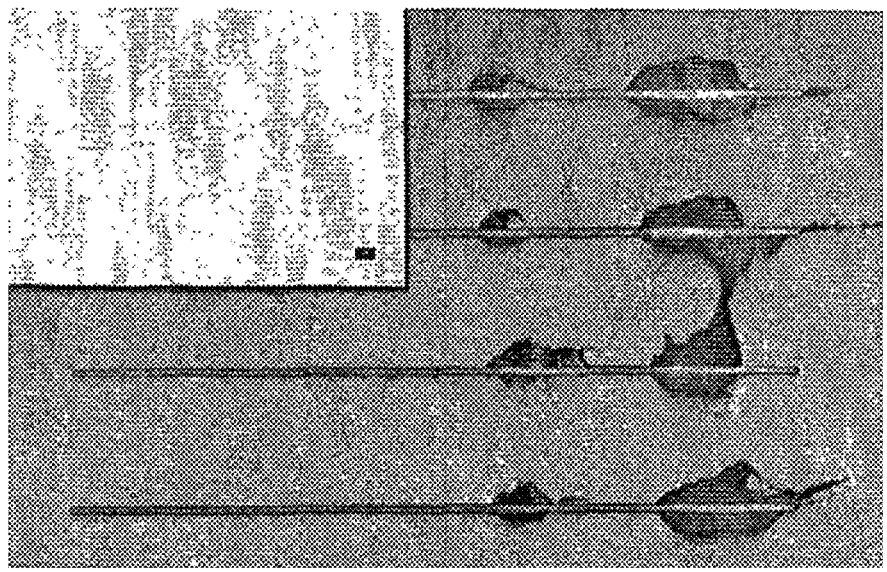
*FIG. 3C*

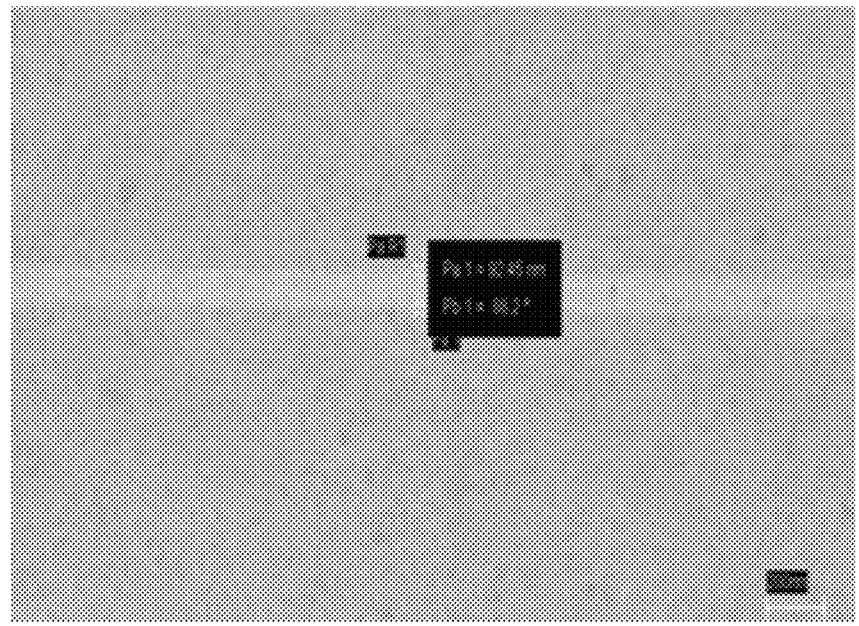
FIG. 7A
FIG. 7C
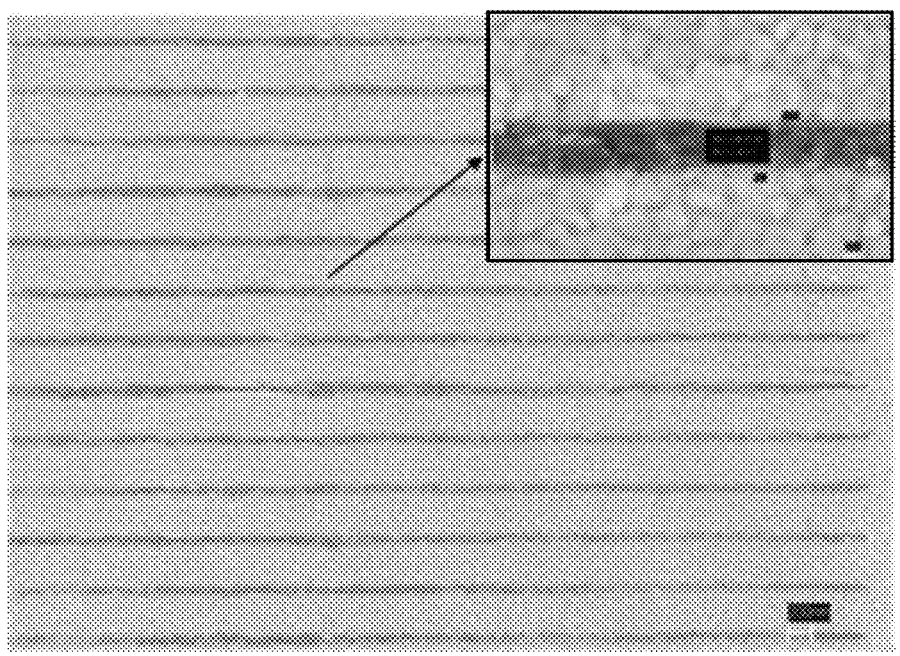
FIG. 7B

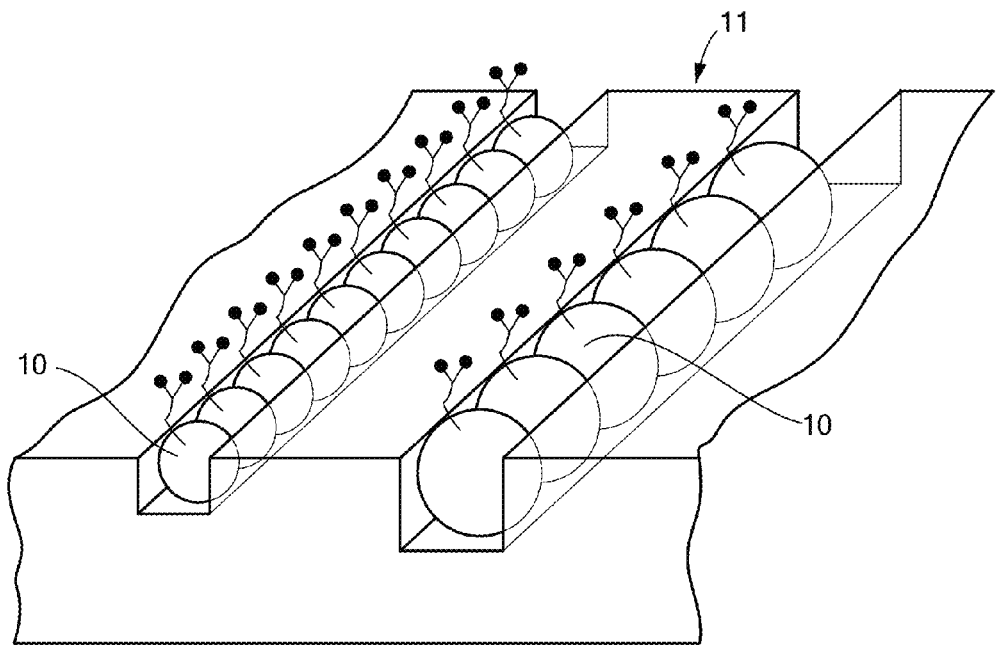
FIG. 11
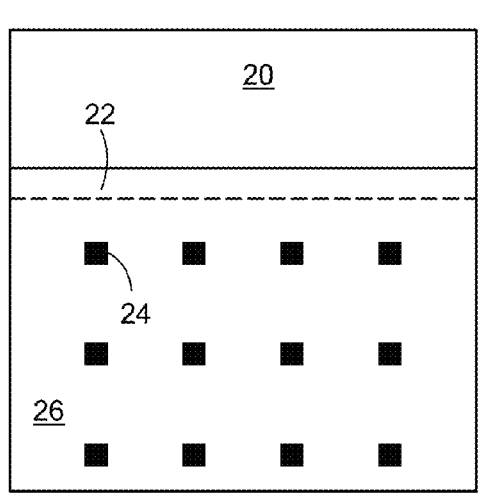 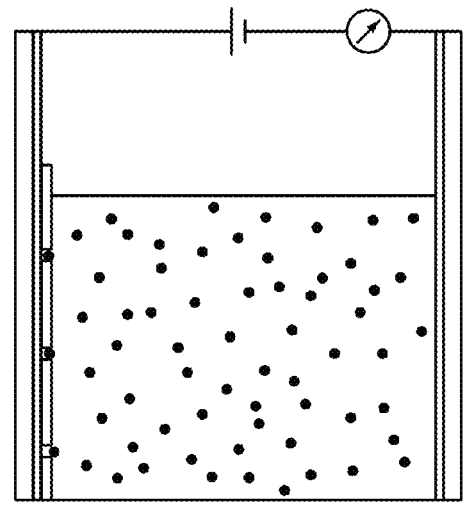
FIG. 12A  FIG. 12B

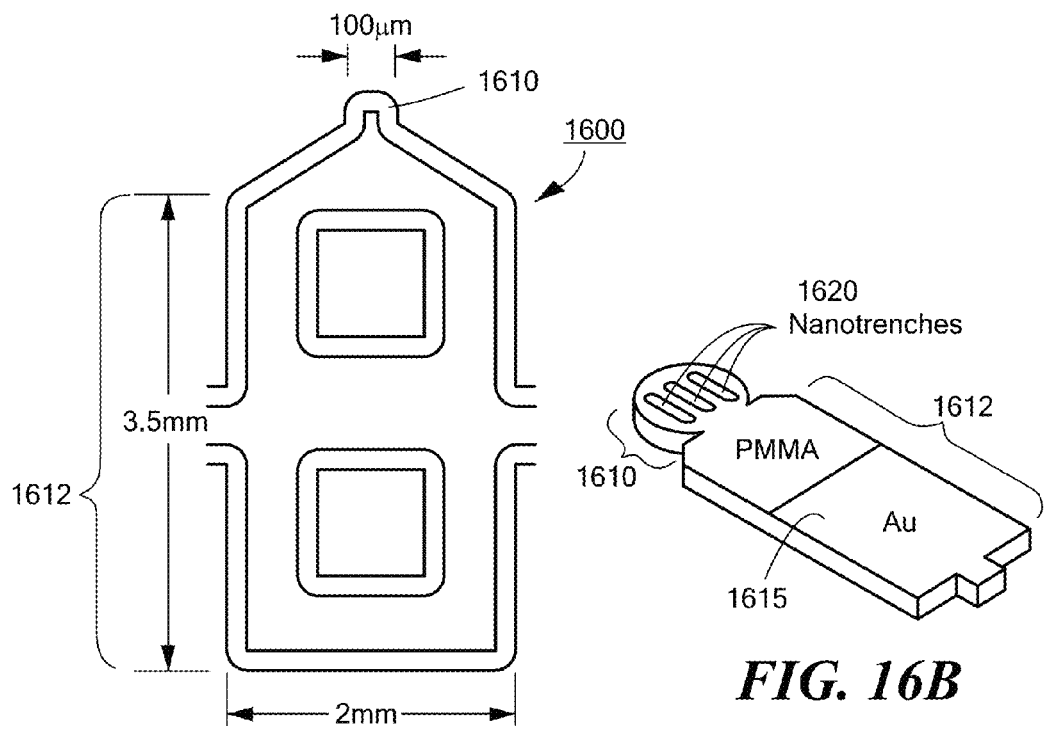
*FIG. 16A*
*FIG. 16B*
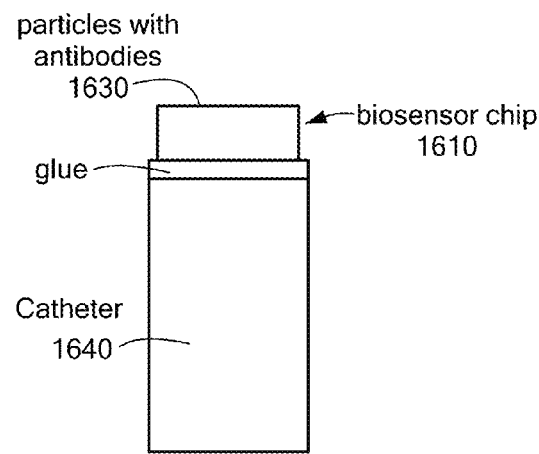
*FIG. 16C*
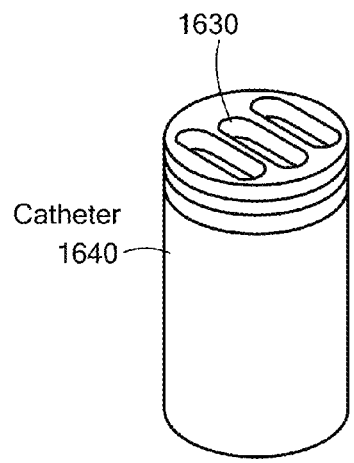
*FIG. 16D*

MULTI-BIOMARKER BIOSENSOR

CROSS-REFERENCE TO RELATED APPLICATIONS

This application claims the benefit of U.S. Provisional Application No. 61/239,145, filed Sep. 2, 2009, and is also a continuation-in-part application of U.S. application Ser. No. 12/085,883, filed Jun. 2, 2008, which was the National Stage of International Application No. PCT/US2006/045911, filed Dec. 1, 2006, which claims the benefit of U.S. Provisional Application No. 60/741,421, filed Dec. 1, 2005, the contents of all of which are hereby incorporated by reference herein.

STATEMENT REGARDING FEDERALLY SPONSORED RESEARCH

The invention was made with support from Grant EEC-0425826 from the National Science Foundation Nanoscale Science and Engineering Center. The United States Government has certain rights in the invention.

FIELD OF THE INVENTION

This disclosure is in the field of medicine, and more specifically, is related to disease screening and detection methods.

BACKGROUND

The fields of nanoscience and nanotechnology generally concern the synthesis, fabrication and use of nanoelements and nanostructures at atomic, molecular and supramolecular levels. The nanosize of these elements and structures offers significant potential for research and applications across the scientific disciplines, including materials science, physics, chemistry, computer science, engineering and biology. Biological processes and methods, for example, are expected to be developed based entirely on nanoelements and their assembly into nanostructures. Other applications include developing nanodevices for use in semiconductors, electronics, photonics, optics, materials and medicine.

One class of nanoelements that has garnered considerable interest consists of carbon nanotubes. P. Teredesai et al., "Pressure-Induced Reversible Transformation in Single-Walled Carbon Nanotube Bundles Studied by Raman Spectroscopy," Chem. Phy. Let., 319, 296-302 (2000). A carbon nanotube has a diameter on the order of nanometers and can be several micrometers in length. These nanoelements feature concentrically arranged carbon hexagons. Carbon nanotubes can behave as metals or semiconductors depending on their chirality and physical geometry.

Although carbon nanotubes have been assembled into different nanostructures, only limited nanotools and fabrication methods for their assembly have been developed. One obstacle has been the manipulation of individual nanoelements, which is often inefficient and tedious. This problem is particularly challenging when assembling complex nanostructures that require selecting and ordering millions of nanoelements across a large area.

Nanostructure assembly has focused on dispersing and manipulating nanoelements using atomic force or scanning tunneling microscopic methods. Although these methods are useful for fabricating simple nanodevices, neither is practical when selecting and patterning, for example, millions of nanoelements for more complex structures. As an alternative, lithographic methods have been developed to modify substrates used for assembling nanoelements. Examples of these lithographic methods include, but are not limited to, electron-beam, ion-beam, extreme ultraviolet and soft lithographies. These methods, however, remain incapable of manipulating individual nanoelements. The development of nanomachines or "nanoassemblers" which are programmed and used to order nanoelements for their assembly holds promise, although there have been few practical advancements with these machines.

Self-assembly is a method for nanodevice fabrication that does not require nanoelements to be individually manipulated. In self-assembly, nanoelements are designed to naturally organize into patterns by atomic, molecular and supramolecular particle interactions. Self-assembled monolayers, for example, are formed by the spontaneous arrangement of molecules into monomolecular layered structures. These structures can be stabilized by van der Waals forces or other forms of noncovalent bonding. Self-assembled monolayers, however, have been problematic when used to transfer nanoelements from one nanosubstrate to a recipient substrate. Although particle interactions can be modified to affect their transport, optical and electrical properties, controlling nanoelement orientation is also a challenge in self-assembly methods. Similarly, nanoscience has been incapable of manipulating particle interactions to reproducibly assemble hundreds of nanodevices.

The advancement of nanotechnology requires millions of nanoelements to be conveniently selected and simultaneously assembled. Nanostructure assembly also requires that nanoelements be ordered across a large area. Previously available methods such as those mentioned above have yet to meet these requirements.

Carbon nanotubes have shown promise as next generation switches or interconnects in electronic applications due to their unique electronic properties. The hindrance to the realization of electronic circuits with carbon nanotubes is the difficulty in positioning and contacting them in a controlled way on a large scale. One method that has been reported in the literature involves spinning a carbon nanotube suspension over a wafer. This produces a random dispersion of carbon nanotubes onto substrates which lack alignment. Another approach utilizes catalytic growth of nanotubes using catalyst particles. Self-assembly on chemically modified surfaces also has been used. These techniques, however, are not suitable for large scale controlled assembly of carbon nanotubes and other nanoelements.

Recently, assembly of carbon nanotubes and nanoparticles on patterned surfaces has been accomplished using electric fields. This process depends on the field generated by the voltage supplied to wires. Assembly of nanoelements works well when using microscale wires to generate the field. However, when the wires are reduced from diameters in the micron range to the nanometer range, their resistance increases by as much as two orders of magnitude. Previous attempts to direct the assembly process using DC electrophoresis with nanowires have failed.

SUMMARY

The invention is based, in part, on the discovery that nanosubstrates can be manufactured to allow detection of biomarkers in vitro and in vivo. Accordingly, in one aspect, the disclosure features a nanosubstrate comprising a substrate layer comprising a photoresist material; a conductive layer deposited on the substrate layer; and an insulating layer deposited on the conductive layer, the insulating layer interrupted by one or more nanotrenches or nanowells.

In some embodiments, the nanosubstrate comprises an area of about 0.005 mm² to about 0.5 mm², about 0.0075 mm² to about 0.25 mm², about 0.01 mm² to about 0.02 mm², or about 0.01 mm² to about 0.01 mm².

In some embodiments, the substrate layer comprises SU-8. In certain embodiments, the substrate layer comprises an area of about 0.005 mm² to about 0.5 mm², about 0.0075 mm² to about 0.25 mm², about 0.01 mm² to about 0.02 mm², or about 0.01 mm² to about 0.01 mm². In particular embodiments, the substrate layer has a thickness of about 10 nm to about 10 µm, of about 20 nm to about 1 µm, of about 30 nm to about 500 nm, of about 40 nm to about 250 nm, of about 50 nm to about 100 nm, or of about 60 nm to about 75 nm.

In some embodiments, the conductive layer comprises an organic or inorganic conductor. In particular embodiments, the conductive layer comprises gold, aluminum, copper, polyanaline, or a combination thereof. In particular embodiments, the conductive layer has a thickness of about 10 nm to about 10 µm, of about 20 nm to about 1 µm, of about 30 nm to about 500 nm, of about 40 nm to about 250 nm, of about 50 nm to about 100 nm, of about 60 nm to about 75 nm, or of about 40 nm to about 100 nm.

In some embodiments, the insulating layer comprises a photoresist material. In particular embodiments, the photoresist material is polymethylmethacrylate. In some embodiments, the insulating layer has a thickness of about 10 nm to about 10 µm, of about 20 nm to about 1 µm, of about 30 nm to about 500 nm, of about 40 nm to about 250 nm, of about 50 nm to about 100 nm, of about 60 nm to about 75 nm, or of about 80 nm to about 150 nm.

In other embodiments, the nanotrenches or nanowells have a width of at least about 20 nm. In particular embodiments, the nanotrenches or nanowells have a width of about 2 nm to about 500 nm, of about 5 nm to about 250 nm, of about 10 nm to about 200 nm, of about 15 nm to about 150 nm, or of about 20 nm to about 100 nm.

In some embodiments, the nanosubstrate further comprises one or more nanoparticles deposited in the one or more nanotrenches or nanowells. In other embodiments, the nanosubstrate comprises two or more nanotrenches or nanowells having different widths. In particular embodiments, the nanoparticles are bound to an antibody or an antigen binding fragment thereof. In some embodiments, the antibody or antigen binding fragment thereof is a 2C5 antibody or an anti-PSA antibody.

In some embodiments, the nanosubstrate further comprises two or more nanoparticles deposited in the two or more nanotrenches or nanowells, the nanoparticles belonging to two or more different size classes, wherein the nanoparticles in each size class have a diameter less than or equal to the width of the nanotrench or nanowell in which they are deposited. In particular embodiments, the nanoparticles of each size class are covalently bound to a different antibody or antigen binding fragment thereof.

In another aspect, the disclosure features a medical device, instrument, or implant comprising a nanosubstrate described herein. In particular embodiments, the medical device, instrument, or implant is a clamp, forceps, tubing, needle, catheter, or endoscope. In certain embodiments, the medical device is an indwelling catheter, such as a urinary catheter, vascular catheter, peritoneal dialysis catheter, or central venous catheter. In some embodiments, a nanosubstrate described herein is attached to a medical device, instrument, or implant using an adhesive, such as a biocompatible adhesive.

In another aspect, the disclosure features a method of preparing a nanosubstrate, comprising providing a first substrate layer; depositing an adhesion layer onto a surface of the first substrate layer; depositing a second substrate layer onto the adhesion layer; depositing a conductive layer onto the second substrate layer; depositing an insulating layer onto the conducting layer; creating a pattern of nanotrenches or nanowells in the insulating layer by lithography; and removing the adhesion layer to release the nanosubstrate, the nanosubstrate comprising the second substrate layer, the conductive layer, and the insulating layer.

In some embodiments, the nanosubstrate comprises an area of about 0.005 mm² to about 0.5 mm², about 0.0075 mm² to about 0.25 mm², about 0.01 mm² to about 0.02 mm², or about 0.01 mm² to about 0.01 mm².

In some embodiments, the first substrate layer comprises silicon, such as a silicon wafer.

In some embodiments, the adhesion layer comprises chromium, titanium, or titanium oxide. In particular embodiments, the adhesion layer has a thickness of about 1 nm to about 50 nm, of about 2 nm to about 40 nm, of about 3 nm to about 20 nm, of about 4 nm to about 10 nm, or of about 3 nm to about 6 nm. In some embodiments, the adhesion layer is deposited by chemical or physical vapor deposition.

In some embodiments, the second substrate layer comprises a photoresist material, such as SU-8. In certain embodiments, the substrate layer comprises an area of about 0.005 mm² to about 0.5 mm², about 0.0075 mm² to about 0.25 mm², about 0.01 mm² to about 0.02 mm², or about 0.01 mm² to about 0.01 mm². In particular embodiments, the substrate layer has a thickness of about 10 nm to about 10 µm, of about 20 nm to about 1 µm, of about 30 nm to about 500 nm, of about 40 nm to about 250 nm, of about 50 nm to about 100 nm, or of about 60 nm to about 75 nm. In certain embodiments, the second substrate layer is deposited by spin coating.

In some embodiments, the conductive layer comprises an organic or inorganic conductor. In particular embodiments, the conductive layer comprises gold, aluminum, copper, polyanaline, or a combination thereof. In particular embodiments, the conductive layer has a thickness of about 10 nm to about 10 µm, of about 20 nm to about 1 µm, of about 30 nm to about 500 nm, of about 40 nm to about 250 nm, of about 50 nm to about 100 nm, of about 60 nm to about 75 nm, or of about 40 nm to about 100 nm. In certain embodiments, the conductive layer is deposited by chemical or physical vapor deposition.

In some embodiments, the insulating layer comprises a photoresist material. In particular embodiments, the photoresist material is polymethylmethacrylate. In some embodiments, the insulating layer has a thickness of about 10 nm to about 10 µm, of about 20 nm to about 1 µm, of about 30 nm to about 500 nm, of about 40 nm to about 250 nm, of about 50 nm to about 100 nm, of about 60 nm to about 75 nm, or of about 80 nm to about 150 nm. In certain embodiments, the insulating layer is deposited by spin coating.

In some embodiments, the lithography is electron beam lithography. In other embodiments, the nanotrenches or nanowells have a width of at least about 20 nm. In particular embodiments, the nanotrenches or nanowells have a width of about 2 nm to about 500 nm, of about 5 nm to about 250 nm, of about 10 nm to about 200 nm, of about 15 nm to about 150 nm, or of about 20 nm to about 100 nm.

In other embodiments, the method further comprises contacting the substrate with an aqueous solution of nanoparticles; and applying a DC voltage between an anode and a cathode, wherein the anode is the conductive layer of the nanosubstrate and the cathode is a conductor placed in the aqueous solution without contacting the nanosubstrate, thereby electrophoretically assembling the nanoparticles within the nanotrenches or nanowells of the nanosubstrate.

In some embodiments, the nanoparticles are covalently bound to an antibody or antigen binding fragment thereof described herein.

In other embodiments, the method further comprises attaching the nanosubstrate to a medical device, instrument, or implant described herein.

In another aspect, the disclosure features a method of detecting a biomarker, comprising providing a nanosubstrate described herein; and contacting the nanosubstrate to a biological sample from a subject, the biological sample comprising a biomarker, and wherein binding of the biomarker to the antibody or antigen binding fragment thereof results in a detectable signal, thereby detecting the biomarker.

In some embodiments, the binding of the biomarker to the antibody or antigen binding fragment thereof is determined by immunoassay, radio-immunoassay, competitive-binding assay, Western Blot analysis, ELISA assay, or immunofluorescence assay.

In some embodiments, the biomarker is PSA, CA125, H1N1 virus, HBV antigen, CD46, or AZGP1. In certain embodiments, the biomarker is a cancer biomarker.

In another aspect, the disclosure features a method of diagnosing a disease or disorder associated with a biomarker in a subject, comprising providing a biological sample from the subject; contacting a nanosubstrate described herein to the biological sample, the nanosubstrate comprising one or more nanoparticles bound to an antibody or antigen binding fragment thereof that specifically binds to the biomarker; and determining the presence or absence of the biomarker within the biological sample by immunoassay, radio-immunoassay, competitive-binding assay, Western Blot analysis, ELISA assay, or immunofluorescence assay. In some embodiments, the nanosubstrate is attached to a catheter.

In some embodiments, an increased level of a biomarker in the biological sample relative to a control sample is indicative of the presence or risk of developing the disease or disorder by the subject. In other embodiments, a decreased level of a biomarker in the biological sample relative to a control sample is indicative of the presence or risk of developing the disease or disorder by the subject.

In some embodiments, the nanosubstrate is contacted to the biological sample in vitro.

In other embodiments, the nanosubstrate is contacted to the biological sample in vivo. In particular embodiments, the nanosubstrate is attached to a catheter, and the biological sample is contacted to the nanosubstrate by insertion into a blood vessel of the subject. In certain embodiments, the catheter is removed, and the presence or absence of a biomarker is determined.

In another aspect, the invention features a system for producing a nanosubstrate described herein. In some embodiments, the system comprises a biosensor microassembly platform described herein.

The following figures are presented for the purpose of illustration only, and are not intended to be limiting.

BRIEF DESCRIPTION OF THE DRAWINGS

FIG. 2A is a schematic representation of a process of making a nanosubstrate. FIG. 2B is a schematic representation of a process of assembly of carbon nanotubes by DC electrophoresis using a patterned nanosubstrate.

FIG. 3A shows a field emission scanning electron micrograph (FESEM) of aligned carbon nanotubes, inside polymethylmethacrylate (PMMA) trenches, made using 5V/cm at pH 8. FIG. 3B (inset in FIG. 3A) shows carbon nanotubes made using the same conditions as in FIG. 3A, after the PMMA layer was removed using acetone. FIG. 3C shows carbon nanotubes made using 3 V/cm at pH 8. FIG. 3D (inset in FIG. 3C) shows carbon nanotubes made using the same conditions as in FIG. 3C, after the PMMA layer was removed using acetone.

FIG. 7 shows the effect of voltage when using 80 nm trenches. In FIG. 7A, 3 V/cm was applied for 1 minute, and in FIG. 7B, 5 V/cm was applied for 1 minute. Scale bars represent 200 nm for FIG. 7A and 20 nm for FIG. 7B.

FIG. 11 schematically depicts an embodiment in which differently sized nanoparticles are assembled into a trench of matching width. Each size class of nanoparticle is bound to a different type of antibody, allowing detection of specific antigen binding.

FIG. 12 shows a schematic illustration of nanoscale electrophoretic deposition of negatively charged nanoparticles onto a PMMA patterned anode nanosubstrate. FIG. 12A shows the nanosubstrate with nanowells. FIG. 12B shows the assembly of nanoparticles into the nanowells.

FIG. 13 shows FESEM images of 10-15 nm wide single nanoparticle lines assembled in 30 nm wide PMMA trenches using 2 V/cm for 90 s.

FIG. 16A is a representation of a fabricated nanosubstrate. FIG. 16B is a schematic representation of a fabricated nanosubstrate. FIGS. 16C and 16D are schematic representations of nanosubstrates attached to a catheter.

DETAILED DESCRIPTION OF INVENTION

Figure 1A:
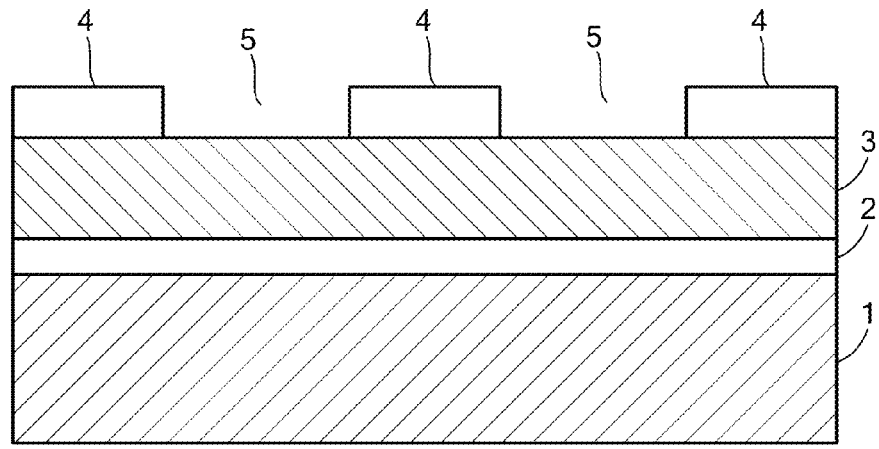
FIG. 1A is a cross-sectional schematic representation of a nanosubstrate embodiment.

All publications, patent applications, patents, and other references mentioned herein are incorporated by reference in their entirety. In case of conflict, the present specification, including definitions, will control. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DEFINITIONS

The articles "a" and "an" are used herein to refer to one or to more than one (i.e., to at least one) of the grammatical object of the article. By way of example, "an element" means one element or more than one element.

The term "or" is used herein to mean, and is used interchangeably with, the term "and/or," unless context clearly indicates otherwise.

The term "about" is used herein to mean a value – or +20% of a given numerical value. Thus, "about 60%" means a value of between 60–(20% of 60) and 60+(20% of 60) (i.e., between 48 and 70).

As used herein, the term "biological sample" refers to a sample obtained from an organism or from components (e.g., cells) of an organism. The sample may be of any biological tissue or fluid, for example, a sample derived from a patient. Such samples include, but are not limited to, blood, blood cells (e.g., white cells), plasma, tissue or fine needle biopsy samples, urine, peritoneal fluid, and pleural fluid, or cells there from. Biological samples may also include sections of tissues such as frozen sections taken for histological purposes.

As used herein, the term "biomarker" of a disease or condition refers to a gene or a gene product that is up- or down-regulated in a biological sample of a subject having the disease or condition relative to a biological sample from like tissue derivation, which gene or gene product is sufficiently specific to the disease or condition that it can be used, optionally with other genes or gene products, to identify or detect the disease or condition. Generally, a biomarker is a gene or a gene product that is characteristic of the disease or condition.

The term "protein" is used interchangeably herein with the terms "peptide" and "polypeptide".

As used herein, a "subject" is a mammal, e.g., a human, mouse, rat, guinea pig, dog, cat, horse, cow, pig, or non-human primate, such as a monkey, chimpanzee, baboon or rhesus.

As used herein, the term "antibody" refers to a polypeptide that includes at least one immunoglobulin variable region, e.g., an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab, F(ab')$_2$, Fd, Fv, and dAb fragments) as well as complete antibodies, e.g., intact immunoglobulins of types IgA, IgG, IgE, IgD, IgM (as well as subtypes thereof). The light chains of the immunoglobulin can be of types kappa or lambda.

As used herein, the terms "coupled", "linked", "fused", and "fusion" are used interchangeably. These terms refer to the joining together of two more elements or components by whatever means, including chemical conjugation or recombinant means.

Nanosubstrates and Fabrication

The present disclosure provides, in part, a method to assemble nanoelements using a patterned nanosubstrate in a controlled and precise manner using DC electrophoresis. This method can assemble nanotubes and nanoparticles, for example, over larger dimensions (cm scale) than previously possible, and in a brief time (minutes). Furthermore, previous techniques required using wires having diameters in at least the micron range for generating the electric field. When wires having diameters in the nanometer range are used, however, their higher resistance decreases the field to the point that nanoelements cannot be assembled. With the methods of the present disclosure, however, nanoscale conductors can be employed to align and assemble nanoelements by DC electrophoresis.

The present disclosure includes a nanosubstrate having a conductive film that drives the patterned assembly of nanoelements using large area films placed at the bottom of a nanotrench or nanowell. Without limiting the invention to any particular mechanism, it is believed that the large area configuration of the conducting film present in the nanosubstrate according to the disclosure provides a resistance comparable to that of a microwire, allowing sufficient field strength for assembly to be driven by DC electrophoresis.

Figure 1B:
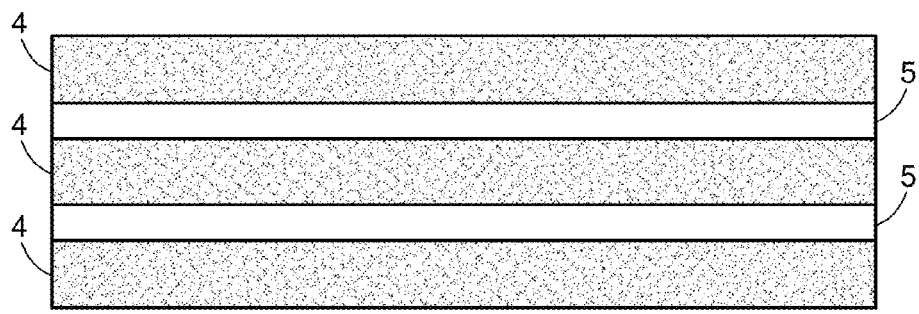
FIG. 1B is a top view schematic representation of the nanosubstrate embodiment of FIG. 1A.

Massive directed assembly of nanoelements by DC electrophoresis is made possible by using nanotrench- or nanowell-based electrical field templates (nanosubstrates). FIGS. 1A and 1B presents schematic representations of an exemplary nanosubstrate of the invention. FIG. 1A shows a cross-section and FIG. 1B shows the surface of the substrate that is exposed to the suspension containing nanoelements for assembly. The base layer of the nanosubstrate is the substrate layer 1. Deposited onto the substrate layer is a thin adhesion layer 2. A conductive layer 3 is in turn deposited onto the adhesion layer. Finally, an insulating layer 4 is deposited onto the conductive layer. The insulating layer is interrupted by one or more nanotrenches 5 or nanowells 5 that allow the conductive layer to be exposed to the solution above the nanosubstrate. The exposed regions of the conductive layer form an electrode for DC electrophoresis. In some instances, this is the anode. The other electrode is placed into the liquid suspension of nanoelements.

Figure 1C:
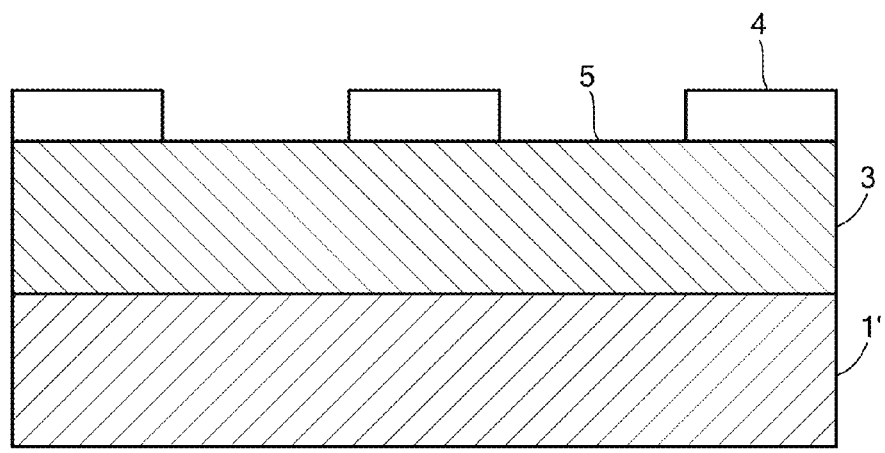
FIG. 1C is a cross-sectional schematic representation of another nanosubstrate embodiment.

FIG. 1C shows an additional exemplary nanosubstrate, in which the conductive layer 3 is deposited onto substrate layer 1', and where the nanosubstrate does not include an adhesion layer.

Nanoelements for use in the invention include, for example, nanocrystals, dendrimers, nanoparticles, nanowires, biological materials, proteins, molecules and organic nanotubes. In certain instances, nanoelements are single walled carbon nanotubes and nanoparticles.

Exemplary nanosubstrates of the disclosure can be made by sequentially depositing an adhesion layer, a conductive layer, and an insulating layer onto the substrate layer, and then removing selected areas of the insulating layer by lithography. See FIG. 2A for a schematic representation of the process. For example, in one embodiment, a 15 mm×15 mm piece of silicon dioxide served as the substrate layer, upon which a 6 nm layer of Cr was deposited as the adhesion layer. A 40 nm layer of Au was deposited onto the Cr layer as the conductive layer. Finally, an 85 nm thick film of PMMA was spun onto the Au layer, followed by electron-beam lithography to make nanoscale trenches in the insulating layer.

Figure 2C:
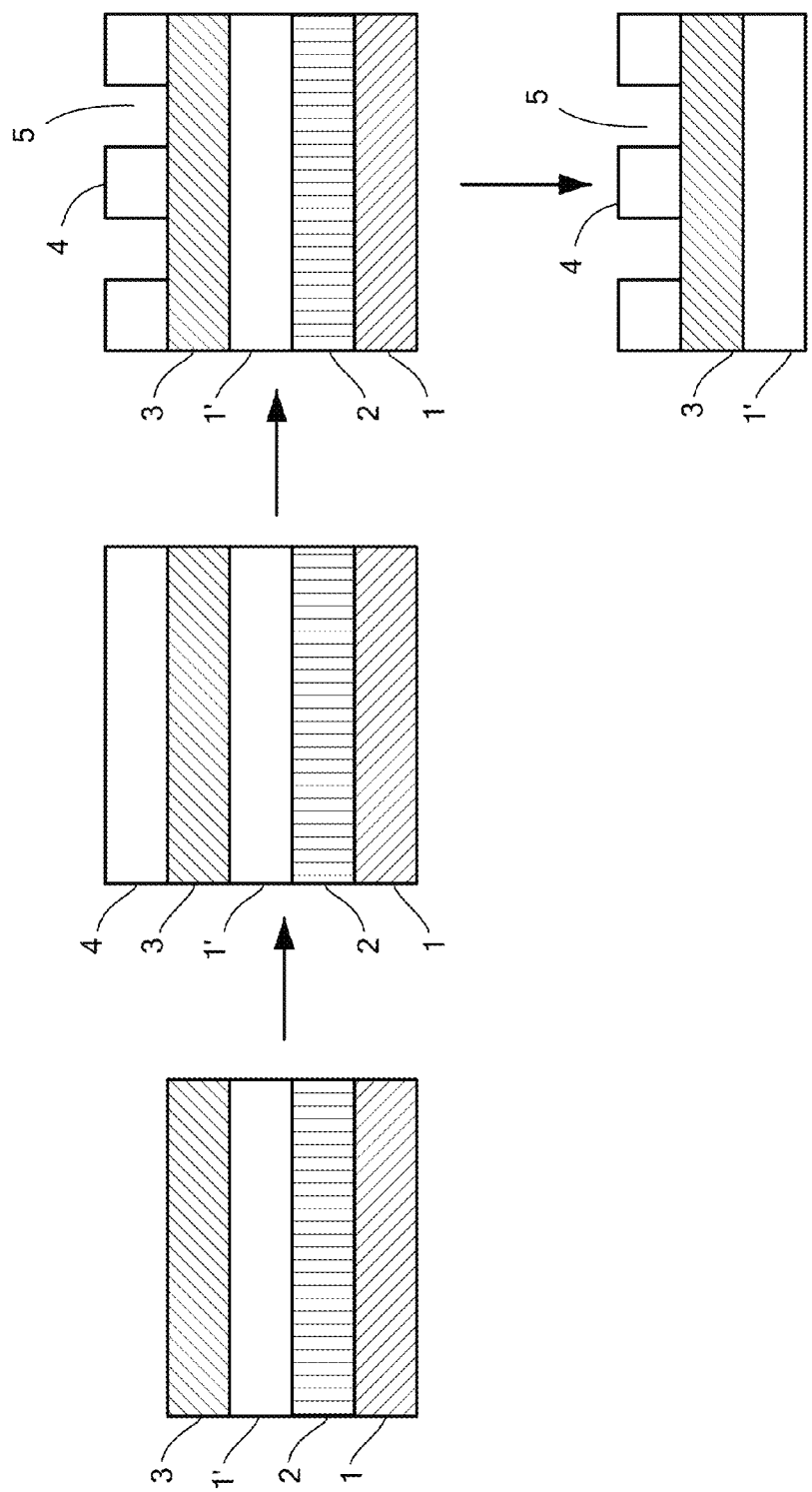
FIG. 2C is a schematic representation of an additional process of making a nanosubstrate.

In certain embodiments, a nanosubstrate of the disclosure does not include an adhesion layer. In such instances, an exemplary nanosubstrate can be made by providing a first substrate layer; sequentially depositing an adhesion layer, a second substrate layer, a conductive layer, and an insulating layer; removing selected areas of the insulating layer by lithography; then removing the adhesion layer to release the nanosubstrate (which includes the second substrate layer, the conductive layer, and the insulating layer) from the first substrate layer. An exemplary process is depicted in FIG. 2C.

The base layer of a nanosubstrate is the substrate layer. The substrate layer typically extends the length and width of the nanosubstrate and provides structural rigidity. The substrate layer supports the other layers which are added to one surface of the substrate layer. The thickness of the substrate layer is not critical for most applications, and can range, for example from about 100 nm to about several cm or more. A wide variety of non-conducting materials can be used for the substrate layer of a nanosubstrate. Silicon wafers, for example, are capable of being used as a substrate layer. A particular material is silicon dioxide ($SiO_2$, also referred to as silicon oxide). Other suitable materials include organic or inorganic insulating materials, e.g., non-conducting oxides. Additional materials include silicon, quartz, a glass wafer, GaSb, SOI, GaAs, GaP, GaN, Ge, InP, ZnO, SiO, CdSe, CdTe, ZnS, ZnSe, ZnTe, and $Al_2O_3$. It is important that the substrate layer be electrically insulating so that it does not provide current leak pathways that might alter the intended electric field distribution for nanoelement assembly. The substrate layer should be structurally rigid so that the nanoscale structural features of the insulating layer are stably preserved with respect to one another. In some instances, the substrate layer of a nanosubstrate has a smooth surface topology. The substrate layer can be formed by available methods for cutting, polishing, molding, or polymerizing suitable materials, as is well known in the art. The substrate layer can have any desired shape or thickness, but in particular instances, it is a thin sheet or film having an approximately flat surface on at least one side upon which the other layers can be deposited. The two-dimensional shape outlined by the surface of the substrate layer that receives the additional layers of the nanosubstrate can be, for example, circular, rectangular, square, irregular, or another shape.

In embodiments where the nanosubstrate does not include an adhesion layer, a first substrate layer can be used during the fabrication process (such as the process depicted in FIG. 2C), which is ultimately removed from a second substrate layer (onto which the conducting layer and the insulating layer are deposited). In such instances, the first substrate layer can be a material described above, such as a silicon wafer. The second substrate layer can be any material, such as a polymer described herein. Nonlimiting exemplary materials for the second substrate layer include photoresist (e.g., SU-8), PDMS and Parylene.

In one embodiment, the substrate layer has three additional layers adsorbed onto one of its surfaces. These layers can be deposited by any method that provides a generally homogeneous, thin layer with good molecular contact and adhesion to adjacent layers. For example, chemical vapor deposition and physical vapor deposition are suitable methods for depositing metals. One nonlimiting method for depositing metals is sputtering. Polymers such as PMMA can be deposited in the liquid state, for example, by spin coating. If appropriate, suitable methods can be employed to harden the polymer layer, e.g., exposure to heat, light, or chemicals.

The adhesion layer is a thin film that promotes the optimal adhesion of the conductive layer to the substrate layer. The adhesion layer therefore serves to prevent the conductive layer from becoming detached or broken during electrophoresis, particularly at higher voltages which can damage or detach the conductive layer. Examples of materials suitable for use in the adhesion layer are chromium, titanium, and titanium oxide. Any material that can be deposited in a thin film and gives strong adhesion between the substrate layer and the conductive layer can be use for the adhesion layer. The adhesion layer is generally less conductive than the conductive layer. The adhesion layer can be any thickness compatible with its role in promoting adhesion of the conductive layer to the substrate layer. In some instances, the adhesion layer is a thin layer, e.g., about 3 nm to about 6 nm thickness. In embodiments where the adhesion layer is removed during the fabrication of a nanosubstrate, the adhesion layer can be removed by known methods, such as etching (e.g., isotropic etching).

The conductive layer establishes a uniform electric field that drives the assembly of nanoelements on the nanosubstrate. Suitable materials for the conductive layer include any highly conductive metals or metal oxides. Nonlimiting, exemplary conductive materials include carbon ink, silver ink, Ag/AgCl ink, copper, nickel, tin, gold, aluminum, or platinum. The conductive layer can be deposited using any known method, such as metal deposition (such as sputtering (e.g., magnetron sputtering), sputter deposition, vapor deposition, thermal spray coating, and ion beam techniques), electrodeposition coating, etching, and self-assembly. The thickness of the conductive layer is chosen in order to minimize resistance, provide adequate conductivity and a uniform electric field, and good adhesion to adjacent layers. For example, the thickness can be in the range of about 50 nm to about 100 nm. An alternative to using a gold or other metallic conductive layer is to use a conductive polymer such as polyanaline. In this way, a completely biocompatible device can be made, such as a sensor or array for implantation in an animal body or for analysis of metal sensitive proteins in vitro or in vivo.

An insulating layer is added onto the conductive layer, followed by lithography (e.g., electron-beam lithography) to make nanoscale trenches (either linear or curved) or nanoscale wells. Nonlimiting, exemplary materials for the insulating layer include PMMA [poly(methyl methacrylate)], ZEP-520A, APEX-E SAL-601, SNR-200, UVN2, UVN30, UV5, and NEB.

Following exposure, a portion of the insulating layer is removed (e.g., PMMA film is dissolved in acetone) and, after rinsing in deionized water, the gold surface is exposed for the electrical connection. The plain conductive gold surface ensures that a uniform potential is applied underneath the patterned insulating layer, and the electric field distribution is controlled by the patterned insulating PMMA film. The patterns of nanotrenches or nanowells formed by lithography leave desired areas of the conductive layer exposed to the fluid environment containing dispersed nanoelements and determine the pattern of alignment and assembly of nanoelements during electrophoresis. This design has the advantage of achieving consistent assembly over a large area wherever the potential and geometric design of nanotrenches or nanowells are the same. Nanotrenches or nanowells are at least about 20 nm in width or diameter. In certain embodiments, the nanotrenches or nanowells are also less than about 100000 nm, about 10000 nm, about 1000 nm, or about 500 nm in width or diameter. Nanotrenches can be at least about 50 nm in length, and in certain embodiments can be at least about 100 nm, about 500 nm, about 1000 nm, about 10000 nm, about 100000 nm or more in length.

In forming the insulating layer, an electrically insulating material either is deposited directly onto the conductive layer in a liquid state. A monomeric material can be used to coat the conductive layer, followed by polymerization of the monomer by any of a variety of methods. These methods include, but are not limited to, free radical polymerization, photopolymerization, anionic polymerization and cationic polymerization. Polymeric liquids also can be used to insulate the conductive layer, for example, by thermal treatment or photocuring. Any insulating material compatible with a suitable lithography process can be used. One particular material is PMMA. The thickness of the insulating layer is sufficient to provide good electrical insulation, so as not to attract charged nanoelements to unintended areas of the nanosubstrate, and will depend on the dielectric properties of the material. The thickness is also compatible with complete removal by lithography to expose the conducting layer. For example, the range of thickness for the insulating layer can be about 80 nm to about 150 nm.

Any lithographic process capable of selectively removing desired areas of the insulating layer and exposing the conductive layer beneath can be used. Nonlimiting processes include electron-beam, ion-beam, ultraviolet, extreme ultraviolet or soft lithographies. Comparable methods such as holographic, nanoimprint, immersion or interference lithographies can also be used. Generally, a nanosubstrate patterned by one of the above methods features surface depressions or recesses, usually in the form of nanotrenches or nanowells, resulting in exposure of the underlying conductive layer.

A variety of patterns can be created by lithography of the insulating layer of a nanosubstrate of the invention, depending on the geometry of the nanoelements being assembled and the desired end product. Nanotrenches are linear depressions that can be straight or curved as well as intersecting or non-intersecting. Nanowells are approximately circular, square, or rectangular depressions. The nanotrenches or nanowells on a given nanosubstrate can have similar dimensions or different dimensions. The assembly by DC electrophoresis of nanoelements on a nanosubstrate is similar regardless of which type of pattern is present in the insulating layer.

Figure 12C:
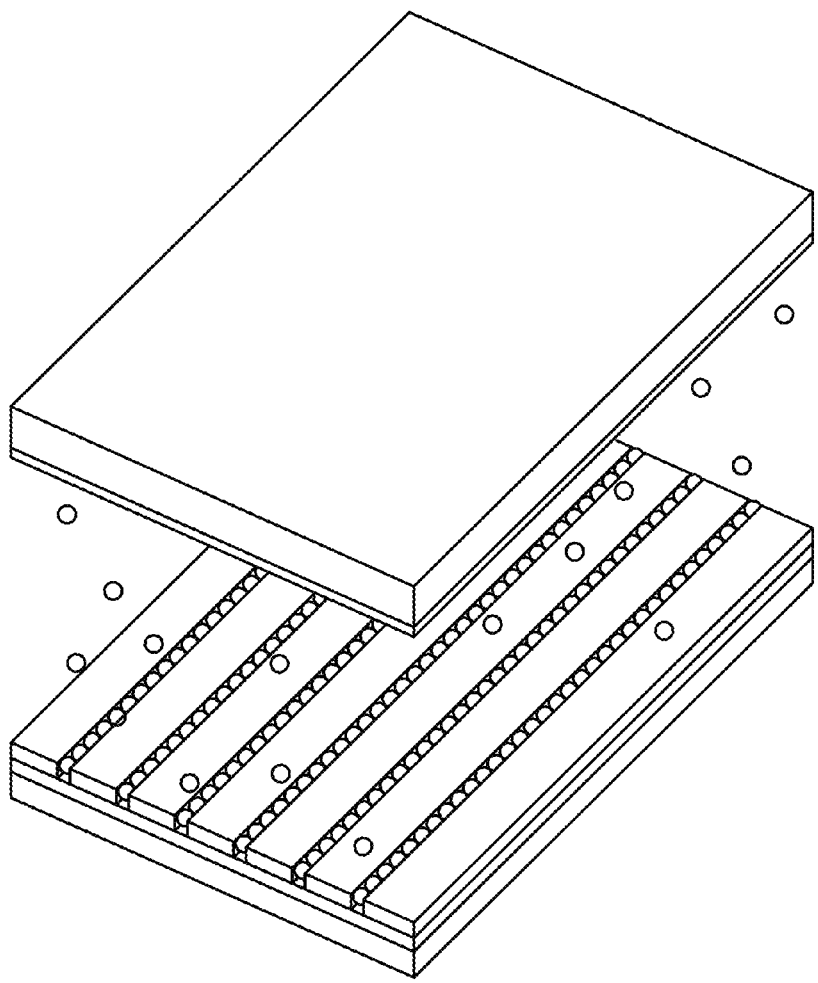
FIG. 12C shows a nanosubstrate having nanotrenches filled with aligned nanoparticles following electrophoresis.

Two different embodiments for the assembly of nanoparticles are depicted in FIG. 12. In the first embodiment, the nanosubstrate 26 shown in FIG. 12A contains an array of nanowells 24 that are submerged in a liquid suspension of nanoparticles up to position 22, such that all of the nanowells are covered by the suspension. A section of the conducting layer 20 is left exposed (i.e., not covered with an insulating layer) for contact with the voltage source. FIG. 12B shows the process of electrophoretic transfer of the nanoparticles from the suspension onto the nanosubstrate (the electrode on the left); another substrate layered with an uninsulated conductive layer serves as the second electrode (right side). In the second embodiment, nanoparticles are assembled into a linear array using the same process, but using a nanosubstrate with nanotrenches instead of nanopores (FIG. 12C).

Lithographically constructed patterns formed on individual nanosubstrates can be combined to make larger patterns. For example, in one embodiment each exposed pattern occupies an area of about 100 μm×100 μm, and combined patterns of 12 such exposures have been made. There is in principle no upper limit to the pattern size, or to the width or length of assembled nanoelements that can be made.

The invention is also directed to methods for directing the assembly of nanoelements such as carbon nanotubes and nanoparticles on structured substrates using DC electrophoresis. The general method is depicted schematically in FIG. 2B. The method employs a nanosubstrate as described above to generate a nanopatterned electric field in a liquid suspension 7 containing charged nanoelements. The field is established by connecting a DC voltage source 8a to the nanosubstrate 9a as one electrode and to a second electrode 9b. Optionally, an ammeter 8b can be used to track current flow during assembly. The field causes the movement by electrophoresis of the nanoelements toward the nanosubstrate. Conditions can be selected such that the nanoelements carry a negative charge, in which case they will migrate toward the anode during electrophoresis. If the conductive layer of the nanosubstrate is chosen as the anode, then nanoelements from the liquid suspension will accumulate and form an assembly 6 on the conductive layer inside the nanotrenches or nanowells formed by the insulating layer. If desired, the assembly can be exposed or removed from the nanosubstrate by eliminating the insulating layer (e.g., dissolving a PMMA layer with acetone and rinsing with deionized water).

Nanoelements can be made of any suitable known material. Nonlimiting materials include, e.g., polystyrene and PLGA polymer (poly(lactic-co-glycolic acid). Nanoelements including carbon nanotubes and PSL or silica nanoparticles typically have a net charge at pH values above or below their isoelectric points. At a pH above the isoelectric point, nanoelements will be negatively charged. Therefore, in some embodiments, the pH of the nanoelement suspension is adjusted to above the isoelectric point of the nanoelements, and the conductive layer of the nanosubstrate is used as the anode and will attract the particles when a voltage is applied. Alternatively, the pH of the suspension can be set to below the isoelectric point of the nanoelements, and the conductive layer of the nanosubstrate is used as the cathode.

Regardless of the polarity of the conductive layer of the nanosubstrate during electrophoresis, the other electrode (second electrode) is placed into the suspension at some known distance from the nanosubstrate. For example, if the conductive layer of the nanosubstrate is the anode, then the cathode will be present in the nanoelement liquid suspension, for example at a distance of about 1 cm removed from the nanosubstrate. It is important to provide a uniform electric field between the conductive layer of the nanosubstrate and the second electrode. This can be accomplished by assuring that the other electrode is equidistant from the nanosubstrate over the full area of the nanosubstrate. For example, if the nanosubstrate is a planar rectangle, then the second electrode should also be planar and arranged parallel to the entire exposed area of the conductive layer of the nanosubstrate. The second electrode can be fabricated of any appropriate conductive material, such as the same material as the conductive layer of the nanosubstrate (e.g., a gold film on a substrate).

In some instances, the nanoelement suspension used as a feed source for assembly can be an aqueous suspension. In other instances, other liquids such as alcohols or other polar solvents can be used, as can mixtures of water and other aqueous solvents. The suspension can contain a sufficient ionic strength such that some level of charge screening occurs at charged positions on the nanoelements. Otherwise, aggregation or nonspecific binding of the nanoelements can occur, which would prevent their orderly assembly at the nanosubstrate. In one embodiment, a small amount of ammonium hydroxide solution, resulting in a final concentration in the range of about 0.5 µM to about 1 µM, is added to a deionized water suspension of nanoelements. This provides both the requisite ionic strength and sets the pH of the solution to the desired range of about 7 to about 8.

The conductive layer of the nanosubstrate is connected to a regulated DC power supply, such as one providing constant voltage adjustable in the range of about 1 V/cm to about 5 V/cm between the electrodes. Electrical connection with the connective layer of the nanosubstrate can be established by a variety of conventional techniques. One suitable method is to leave a portion of the conductive layer exposed (i.e., without any overlaying insulating layer) at an edge of the nanosubstrate so that electrical contact with the conductive film can be made. In general, the stronger the electric field, the more rapid assembly will take place. A threshold voltage may exist below which no assembly occurs, and too high a voltage will lead to breakdown of the conductive layer with subsequent disruption of assembly. Smaller dimensions of the nanotrenches or nanowells generally requires a higher voltage to drive assembly. An appropriate voltage for a given set of conditions is readily determined by trial.

An embodiment of the invention is a method of making an assembly comprising nanoelements of two or more different size classes. A nanosubstrate is fabricated with nanotrenches or nanopores of two or more different widths. Nanoelements of different size classes are assembled on the nanosubstrate in decreasing order of size. In each cycle, nanoelements of a size class are assembled in a nanotrench or nanopore of similar or slightly greater size as the average width or diameter of the nanoelements. In that way, each size class of nanoelements can be targeted to one or more specific nanotrenches or nanopores. In certain embodiments, nanoelements belonging to different size classes can be differentially functionalized, resulting in spatially distributed chemical groups that can be employed, for example, as an array or biosensor. For example, in the embodiment depicted in FIG. 11, two different size classes of nanoparticles 10 are assembled in nanotrenches of different widths. Each of the nanoparticle classes has been functionalized and bound to a different type of antibody or fragment of an antibody. When an antigen 11 is present which binds to one of the antibody types, but not the other, a specific signal is generated that indicates the presence and identity of the antigen. For example, a second antibody that binds to the antigen and possesses a bound label, such as a fluorescent tag or an enzyme, can be used to detect antigens bound to the nanosubstrate.

Antibodies can be attached to nanoparticles described herein using standard methods. For example, nanoparticles can be functionalized on their surface with $-NH_2$, $-CH_2Cl$, $-CHO$ (aldehyde), $-OSO_2CH_6H_4-CH_3$, $-CHOCH_2$ (epoxide), biotin, and avidin.

Figure 15:
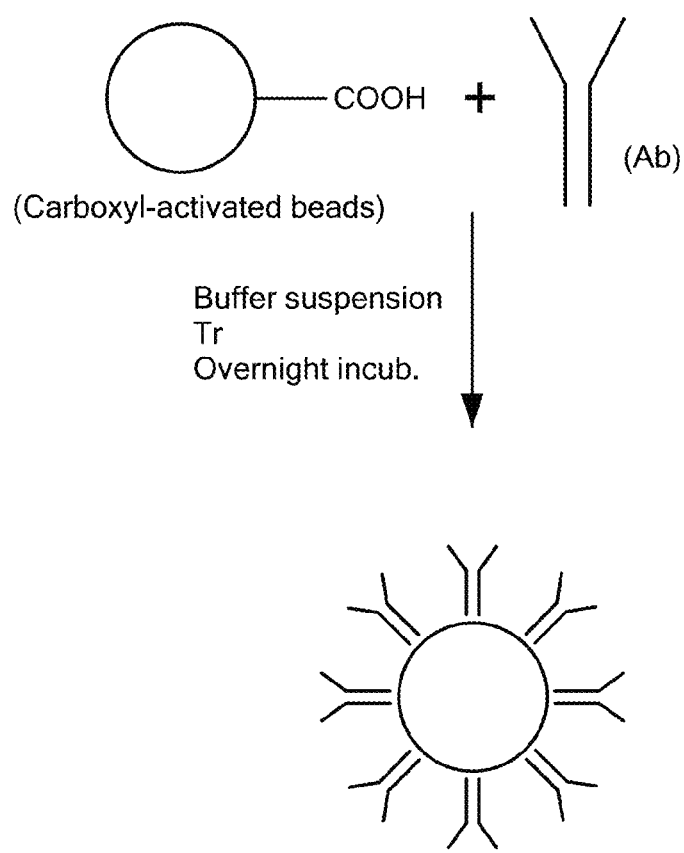
FIG. 15 is a schematic representation of an antibody coating process.

FIG. 15 depicts one exemplary method for attaching an antibody to a nanoparticle. First, a polystyrene bead is functionalized on its surface with a $-COOH$ group. Next, an antibody is incubated with the functionalized nanoparticle suspended in a saline buffered solution, such as overnight. Unbound antibody can then be removed from the bead suspension by ultracentrifugation for, e.g., 15 minutes at 12×1000 rpm.

Any antibody, or antigen-binding portion thereof, can be attached to a nanoparticle described herein. Exemplary antibodies include, without limitation, mAb-2C5 (Iakoubov et al. (1997) *Oncol. Res.* 9:439-446), mAb to carcinoembriogenic antigen (Hammarstrom (1999) *Semin. Cancer Biol.* 2:67-81), or antibodies that bind to biomarkers such as PSA (prostate specific antigen), CA125 (ovarian cancer antigen), H1N1 virus, HBV antigen (hepatitis B virus), CD46 (membrane cofactor protein to malignant neoplasm of prostate, bacterial infections, astrocytoma, glioblastoma, gonorrhoeae), and AZGP1 (alpha-2-glycoprotein to cardiac hypertrophy, *E. coli* infection to Central Nervous System). Antigen-specific binding portions of antibodies can also be used, such as Fab, Fab'2, and Fv, and the antibodies may be genetically engineered or naturally produced using known methods. Alternatively, other binding agents specific for the disease markers may be used.

Methods of Using Nanosubstrates as Biosensors

The nanosubstrates described herein can be used to detect the level of a biomarker, such as a polypeptide or other antigen, in a biological sample from a subject. Exemplary biological fluids include, but are not limited to, blood, plasma, lacrimal secretions, saliva, seminal fluid, vaginal secretion, sweat, mucous, or urine. In some instances, the nanosubstrate is contacted with the biological fluid and then post-processed for the detection of binding of a biomarker to an antibody on a nanoparticle on the nanosubstrate.

The detection of a biomarker can be performed using methods known in the art. Such assay methods include, but are not limited to, immunoassays, radio-immunoassays, competitive-binding assays, Western Blot analysis, ELISA assays, and immunofluorescence assays.

In certain instances, an elevated level of a biomarker relative to a control indicates a risk of disease or disorder. In other instances, a reduced level of a biomarker relative to a control indicates a risk of disease or disorder.

In some instances, a biomarker is detected after separation from a biological sample. Separation techniques include, but are not limited to, column chromatography, filtration, ultrafiltration, salt precipitation, solvent precipitation, solvent extraction, distillation, immunoprecipitation, SDS-polyacrylamide gel electrophoresis, isoelectric point electrophoresis, dialysis, and recrystallization.

For chromatography, affinity chromatography, ion-exchange chromatography, hydrophobic chromatography, gel filtration, reverse phase chromatography, adsorption chromatography, and such may be used (see, e.g., *Strategies for Protein Purification and Characterization: A Laboratory Course Manual*. Ed, Daniel R. Marshak et al., Cold Spring Harbor Laboratory Press (1996)). These chromatography procedures can also be liquid chromatography, such as HPLC and FPLC.

In some instances, the presence of biomarkers in a biological sample can be measured by optionally modifying or partially degrading the proteins in a biological sample, for example, by treating the biological sample with an appropriate protein modification enzyme before separation. Such a modification or partial degradation can be utilized when, for example, the proteins in a biological sample are not easily separated. Such protein modification enzymes include, for example, trypsin, chymotrypsin, lysylendopeptidase, protein kinase, and glucosidase.

In certain instances, multidimensional separation techniques, such as tryptic peptide fractionation using reversed phase and ion exchange LC, or protein pre-fractionation methods, like ion exchange, size exclusion, hydrophobic interaction and various affinity methods, can be used (Martosella, et al., *J. Proteome Res*. (2005) 4:1522-1537). One nonlimiting example of a pre-fractionation method includes removing high abundance proteins to reduce the dynamic range of protein levels in biological fluids to better match that of the analytical platform.

A variety of depletion methods for specific removal of high abundance proteins from bodily fluids can be used (see, e.g., Govorukhina, et al., *J. Chromatogr. A* (2003) 1009:171-178). A nonlimiting example is the multiple affinity removal system (MARS, Agilent, Palo Alto, Calif.), which utilizes an affinity column. This column can deplete albumin, IgG, IgA, transferrin, haptoglobin and antitrypsin in human plasma (Ogata, et al., *J. Proteome Res*. (2005) 4:837-845; Bjorhall, et al., Proteomics (2005) 5:307-317). The MARS column can deplete these proteins from 30-40 µl of plasma at a time and can be regenerated up to 200 times.

Another separation technique that can be used in the methods disclosed herein involves using a combination of three lectins in the form of a multi lectin column (M-LAC). This affinity column can capture and enrich fractions, e.g., glycoprotein fractions, in plasma. In some instances, fractions can be subjected to LC-MS after tryptic digestion (Yang, et al., *J. Chromategr. A* (2004) 1053:79-88).

Methods of Assembly of Biosensors for In Vivo Applications

For in vivo applications, a nanosubstrate described herein can be attached to the top of a medical device, such as a catheter, and subsequently inserted into a subject for contacting in vivo a biomarker with the nanosubstrate. FIG. 16 illustrates an exemplary biosensor device and a process for attaching the device onto a medical device.

As depicted in FIG. 16, an elongated biosensor 1600 can be fabricated using a method described herein to include a nanosubstrate 1610 at a terminal end of nanosubstrate holder 1612. Nanosubstrate 1610 includes substrate 1615, trenches 1620, and nanoparticles 1630 within trenches 1620. Nanosubstrate 1610 is attached to a terminal end of catheter 1640 by affixing substrate 1615 to catheter 1640, with nanoparticles 1630 exposed at the terminal end of catheter 1640. Substrate 1615 can be affixed to catheter 1640 by any known means, such as the use of an adhesive (e.g., a biocompatible adhesive). After nanosubstrate 1610 is affixed to catheter 1640, nanosubstrate holder 1612 is removed from nanosubstrate 1610, leaving nanosubstrate 1610 affixed to catheter 1640.

Figure 17:
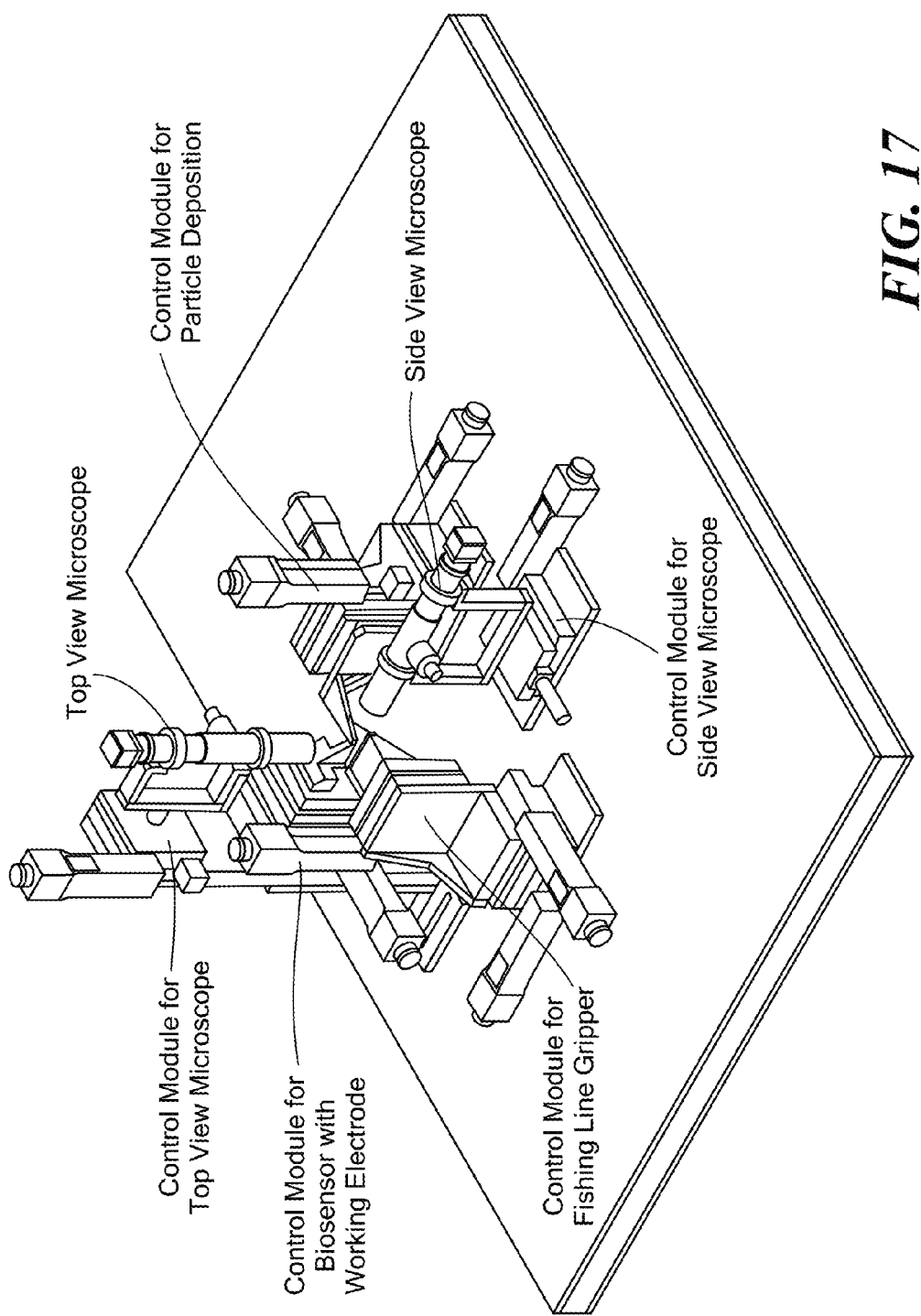
FIG. 17 is a schematic representation of a high precision motion control and visual feedback system for fabricating nanosubstrates.

In certain instances, the assembly and attachment of a nanosubstrate to a catheter are carried out on a system having high precision motion control and visual feedback, such as controlled by computers. A schematic diagram of one nonlimiting representative system is shown in FIG. 17. Assembly of an in vivo nanosubstrate followed by attachment of the catheter to the substrate layer of the nanosubstrate can be conducted according to the following steps: (1) initializing the system to the home position; (2) depositing a high viscosity glue onto the top of a smoothly cut catheter by bringing a needle into contact with the catheter; (3) gluing the nanosubstrate to the catheter utilizing a biocompatible glue; (4) selectively assembling antibody coated nanoparticles into the nanotrenches of the nanosubstrate as detailed above; and (5) breaking the nanosubstrate holder and storing the in vivo biosensor for testing.

Methods of Using Biosensor Devices for Diagnosis

The biosensor devices described herein can be used to identify a subject having, or at risk of developing, a disease or disorder. Certain methods include obtaining a biological sample from a subject and a sample from a control subject not having, or not at risk of developing, the disease or disorder, and contacting a biosensor device with the biological samples. The biological sample can be, e.g., urine, blood, serum, plasma, saliva, semen, a vaginal secretion, or cerebrospinal fluid. In some instances, the biological sample is a plasma sample.

In other methods, a biosensor device described herein can be inserted into a subject, and the biosensor device contacts one or more biomarkers in vivo. For example, a biosensor device, such as a biosensor device attached to a catheter, can be inserted into the body of a subject, such as a blood vessel, of the subject. The biosensor device can then be removed from the subject and the level of one or more biomarkers can be detected as described herein. In particular instances, a biosensor device can be used to detect the level of a plurality of biomarkers, such as 2, 3, 4, 5, 6, 7, 8, 9, 10, 20, 30, 40, 50, 100, 250, 500, 750, 1000 biomarkers, or more.

Any known biomarker can be used to identify a subject having, or at risk of developing, a disease or disorder. If the level of one or more of these biomarkers is different relative to the control level, the subject can be classified as having, or at risk of developing, a disease or disorder associated with the biomarker.

For example, the level of one or more of the following biomarkers can be measured: PSA (prostate specific antigen), CA125 (ovarian cancer antigen), H1N1 virus, HBV antigen (hepatitis B virus), CD46 (membrane cofactor protein to malignant neoplasm of prostate, bacterial infections, astrocytoma, glioblastoma, gonorrhoeae), and AZGP1 (alpha-2-glycoprotein to cardiac hypertrophy, *E. coli* infection to Central Nervous System). Other biomarkers are described in, e.g., U.S. Pat. Nos. 7,666,583 and 7,537,938.

Yet other biomarkers are nucleohistones (NHS) and carcinoembryonic antigen (CEA), which are two of the many biomarkers that are pathologically indicated in diseased or cancerous condition. NHS is found in diseases such as Systemic Lupus Erythematosus (SLE), and CEA is found in various cancerous conditions such as colorectal, gastric, pancreatic, lung and breast carcinomas. NHS are classic biomarkers that are released by most carcinomas and are not associated with a particular type of cancer.

Once a subject is identified as having, or at risk of developing, a disease or disorder, the subject can be treated with an appropriate therapy for the condition.

Diseases/Disorders

The biosensor devices described herein can be used to diagnose many types of diseases or disorders.

In particular instances, a biosensor device is used to diagnose hyperproliferative, hyperplastic, metaplastic, dysplastic, or pre-neoplastic diseases or disorders.

By "hyperproliferative disease or disorder" is meant a neoplastic cell growth or proliferation, whether malignant or benign, including all transformed cells and tissues and all cancerous cells and tissues. Hyperproliferative diseases or disorders include, but are not limited to, precancerous lesions, abnormal cell growths, benign tumors, malignant tumors, and cancer. Additional nonlimiting examples of hyperproliferative diseases, disorders, and/or conditions include neoplasms, whether benign or malignant, located in the prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, or urogenital tract.

As used herein, the term "tumor" or "tumor tissue" refers to an abnormal mass of tissue that results from excessive cell division. A tumor or tumor tissue comprises "tumor cells", which are neoplastic cells with abnormal growth properties and no useful bodily function. Tumors, tumor tissue, and tumor cells may be benign or malignant. A tumor or tumor tissue can also comprise "tumor-associated non-tumor cells", such as vascular cells that form blood vessels to supply the tumor or tumor tissue. Non-tumor cells can be induced to replicate and develop by tumor cells, for example, induced to undergo angiogenesis within or surrounding a tumor or tumor tissue.

As used herein, the term "malignancy" refers to a non-benign tumor or a cancer. As used herein, the term "cancer" means a type of hyperproliferative disease that includes a malignancy characterized by deregulated or uncontrolled cell growth. Examples of cancer include, but are not limited to, carcinoma, lymphoma, blastoma, sarcoma, and leukemia or lymphoid malignancies. More particular examples of such cancers are noted below and include squamous cell cancer (e.g., epithelial squamous cell cancer), lung cancer (including small-cell lung cancer, non-small cell lung cancer, adenocarcinoma of the lung and squamous carcinoma of the lung), cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer, uterine carcinoma, salivary gland carcinoma, kidney or renal cancer, prostate cancer, vulval cancer, thyroid cancer, hepatic carcinoma, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to, Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Fibrosarcoma, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, and Wilm's Tumor.

The methods described herein can also be used to diagnose premalignant conditions, e.g., to prevent progression to a neoplastic or malignant state including, but not limited to, those disorders described above. The methods described herein can further be used to diagnose hyperplastic disorders. Hyperplasia is a form of controlled cell proliferation, involving an increase in cell number in a tissue or organ, without significant alteration in structure or function. Hyperplastic disorders include, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, focal epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia.

The methods described herein can also be used to diagnose metaplastic disorders. Metaplasia is a form of controlled cell growth in which one type of adult or fully differentiated cell substitutes for another type of adult cell. Metaplastic disorders include, but are not limited to, agnogenic myeloid metaplasia, apocrine metaplasia, atypical metaplasia, autoparenchymatous metaplasia, connective tissue metaplasia, epithelial metaplasia, intestinal metaplasia, metaplastic anemia, metaplastic ossification, metaplastic polyps, myeloid metaplasia, primary myeloid metaplasia, secondary myeloid metaplasia, squamous metaplasia, squamous metaplasia of amnion, and symptomatic myeloid metaplasia.

The methods described herein can also be used to diagnose dysplastic disorders. Dysplasia can be a forerunner of cancer and is found mainly in the epithelia. Dysplasia is a disorderly form of non-neoplastic cell growth, involving a loss in individual cell uniformity and in the architectural orientation of cells. Dysplastic cells can have abnormally large, deeply stained nuclei, and exhibit pleomorphism. Dysplasia can occur, e.g., in areas of chronic irritation or inflammation. Dysplastic disorders include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of the jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, ophthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders that can be diagnosed by the methods described herein include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

EXAMPLES

Example I

Manufacturing a Nanosubstrate for Carbon Nanotube Assembly

A 5 nm layer of Cr was deposited by sputtering onto an oxidized silicon surface. A 50 nm layer of Au was then deposited by sputtering over the Cr layer. A 150 nm thick PMMA layer was then spun over the surface. Electron beam lithography was used to pattern nanotrenches of various sizes (see subsequent examples) in the PMMA layer. Following exposure, the substrate was developed resulting in the formation of nanotrenches on the PMMA film exposing parts of the gold surface.

Example II

Assembly of Carbon Nanotube Bundles

The nanosubstrate from Example I was immersed in a 10 ml suspension of 0.01 wt/vol % single wall carbon nanotubes (SWNT) in deionized water. The SWNT were obtained from Carbon Nanotechnologies, Inc. (Houston, Tex.). The pH of the solution was adjusted to 8 by adding ammonium hydroxide solution (final concentration approximately 1 µM). A clean gold substrate placed at a distance of 1 centimeter from the PMMA substrate acted as the cathode. A DC voltage was applied between the two electrodes for 60 seconds, and the current was monitored using a pico-ammeter. An electric field of either 5 V/cm (FIG. 3A) or 3 V/cm (FIG. 3C) resulted in the negatively charged nanotubes being assembled inside the trenches wherever the gold layer was exposed. There were some nanotubes protruding out of the trench, especially at the edges, but these were removed after the PMMA was dissolved (see below).

Following assembly, the PMMA film was stripped using acetone. After removing the PMMA layer, the nanotubes remained intact on the gold surface and oriented in the same location as they were assembled, as shown in FIGS. 3B and 3D.

Figures 3E, 3F:
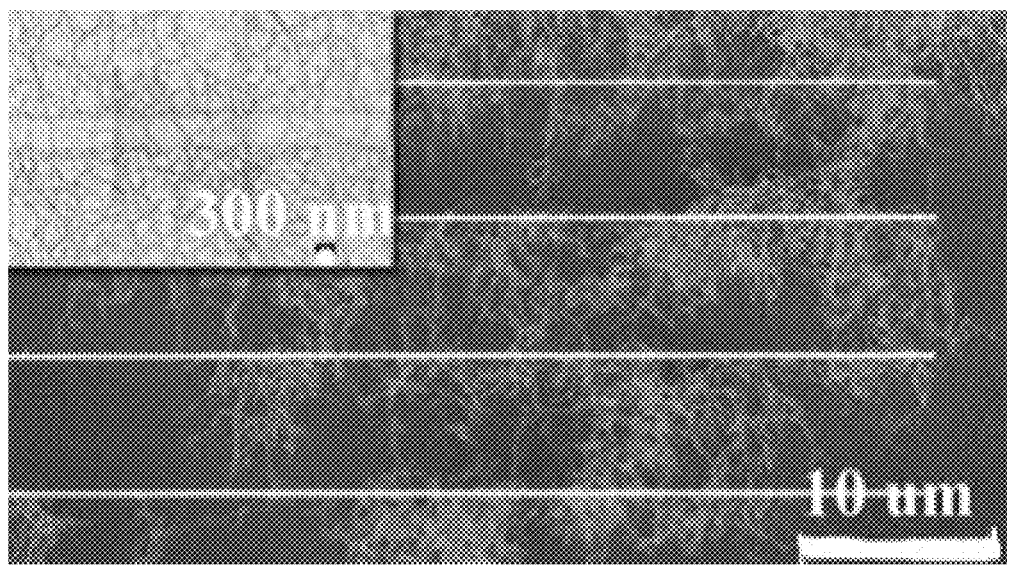
FIG. 3E shows carbon nanotubes made using 3 V/cm in isopropyl alcohol.
FIG. 3F (inset in FIG. 3E) shows carbon nanotubes made using the same conditions as in FIG. 3E, after the PMMA layer was removed using acetone.
Figure 4A:
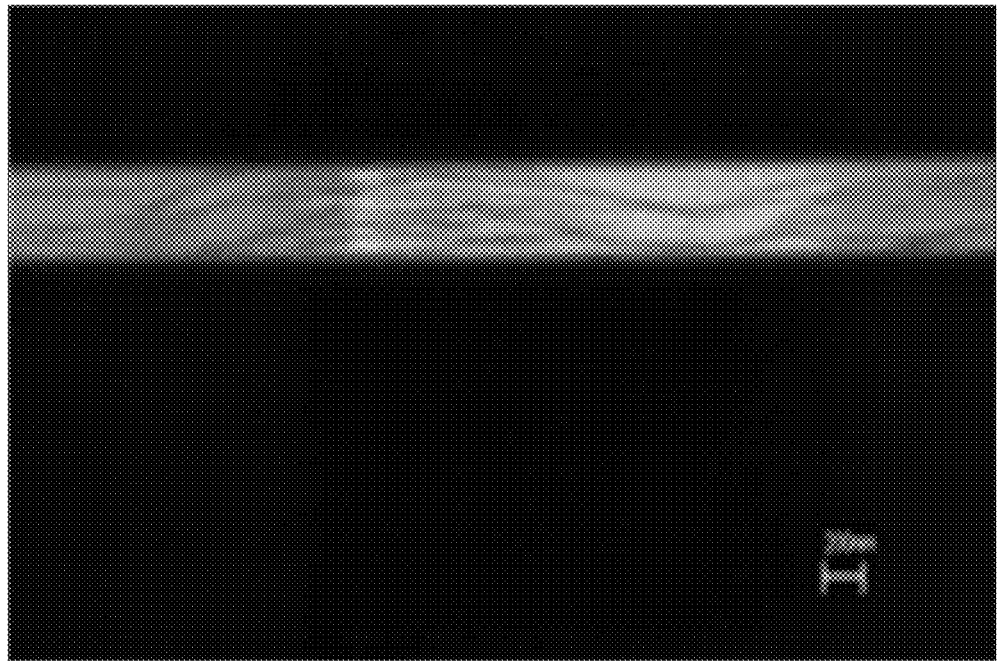
FIG. 4A shows assembled SWNT inside a 250 nm trench.
Figure 4B:
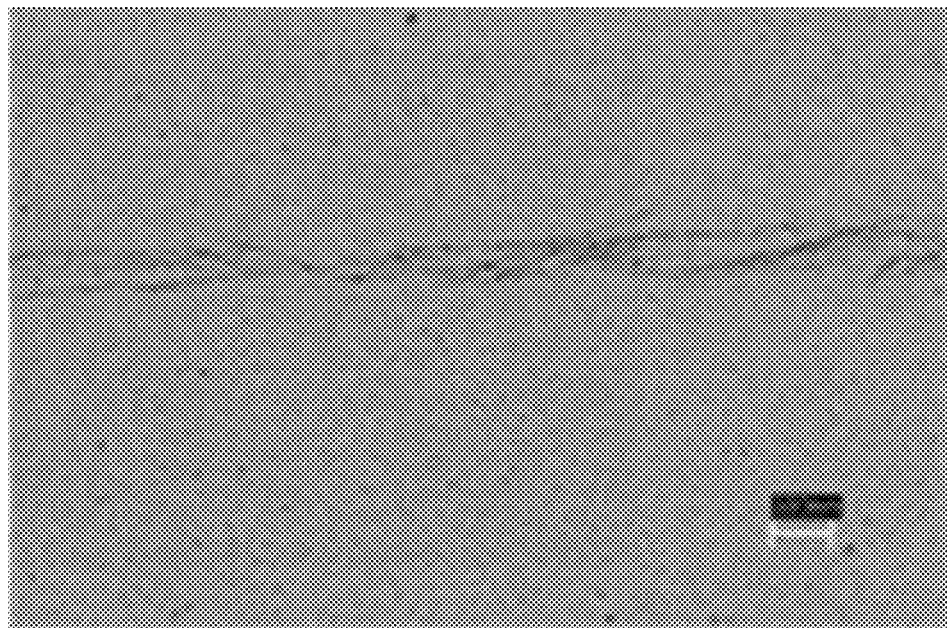
FIG. 4B shows the nanotube bundle after dissolving the PMMA layer with acetone. Assembly was carried out at 3 V/cm. Scale bars represent 200 nm.

When isopropyl alcohol (IPA) was used in place of deionized water for the suspension of nanotubes, electrophoresis for 60 seconds at 3 V/cm did not result in assembly of nanotube bundles within the nanotrenches. As seen in FIG. 3E (and FIG. 3F following PMMA dissolution with acetone), the nanotubes remained disoriented and distributed across the surface of the nanosubstrate. This might be due to the tendency of nanotubes to agglomerate in IPA.

Example III

Effect of Trench Width on Assembly of Carbon Nanotubes

To investigate the effect of trench width on assembly, nanosubstrates were fabricated with 70 μm long trenches having widths of approximately 350 nm, 250 nm, 150 nm, 100 nm and 50 nm. As seen from the results presented in FIGS. 4-7, the density of nanotubes assembled inside the trenches decreased with the width of the trenches for a given voltage.

Example IV

Effect of Voltage on Assembly of Carbon Nanotubes

Figure 5A:
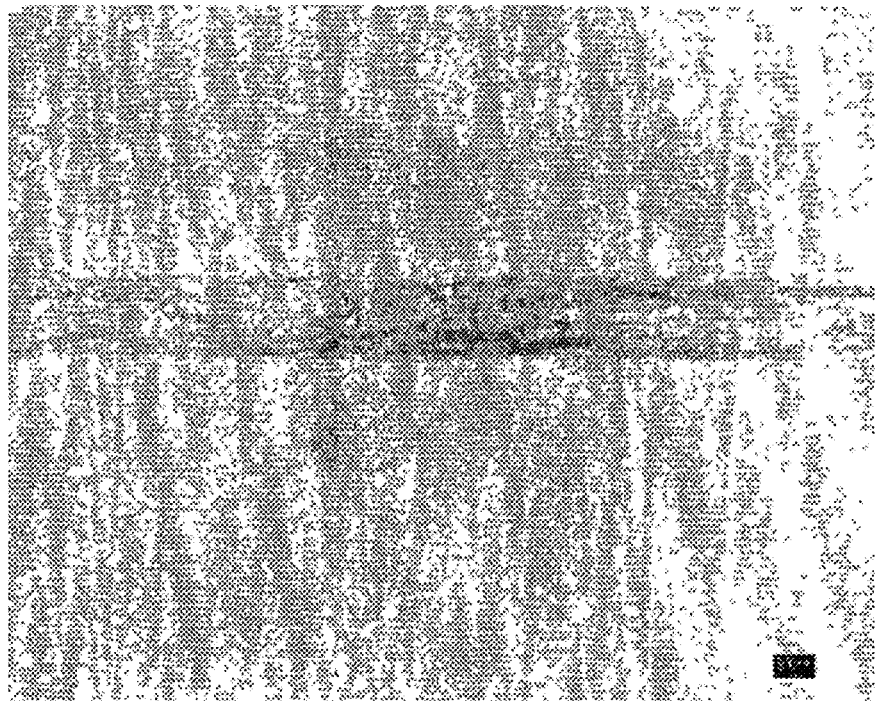
In FIG. 5A assembly was driven at 5 V/cm, and in FIG. 5B assembly was driven at 3 V/cm, both using 250 nm wide trenches. Scale bars represent 200 nm.
Figure 5B:
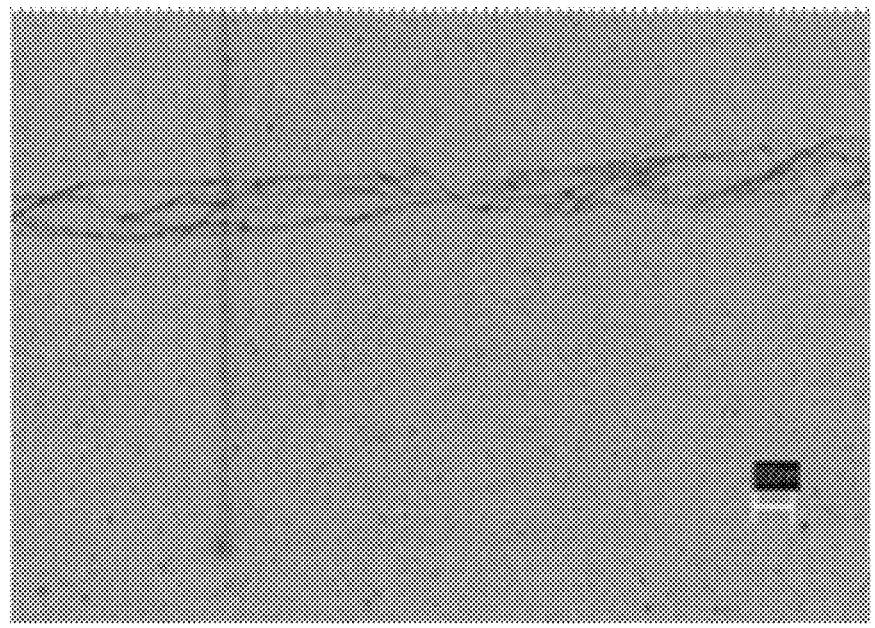
FIG. 5 shows the effect of voltage on the assembly of SWNT.
Figure 6A:
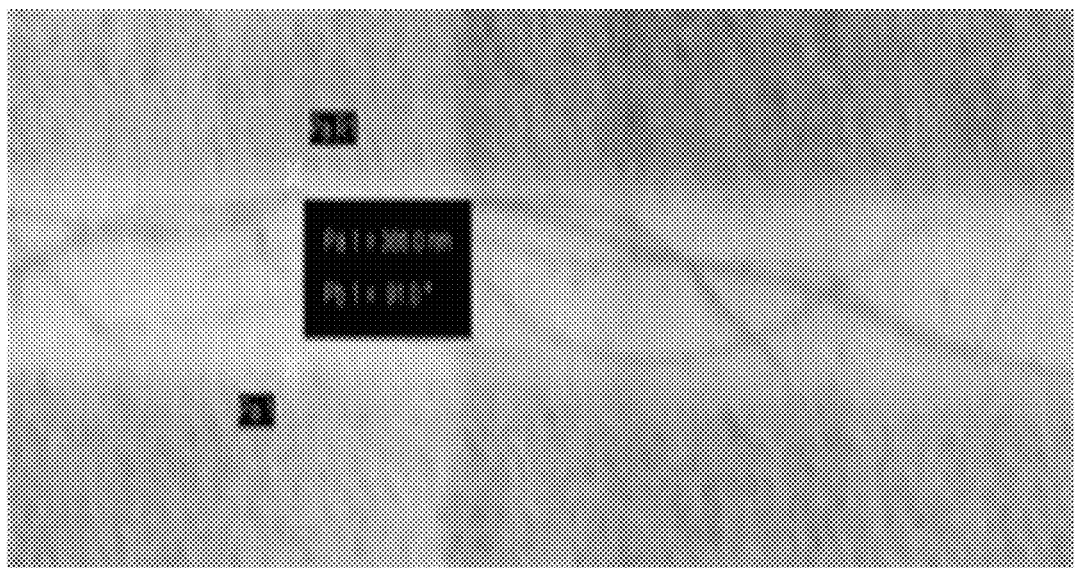
FIG. 6 shows the effect of trench size (trench width 350 nm in FIG. 6A and 140 nm in FIG. 6B). The voltage in each case was 3 V/cm. Scale bars represent 300 nm for FIG. 6A and 200 nm for FIG. 6B.
Figure 6B:
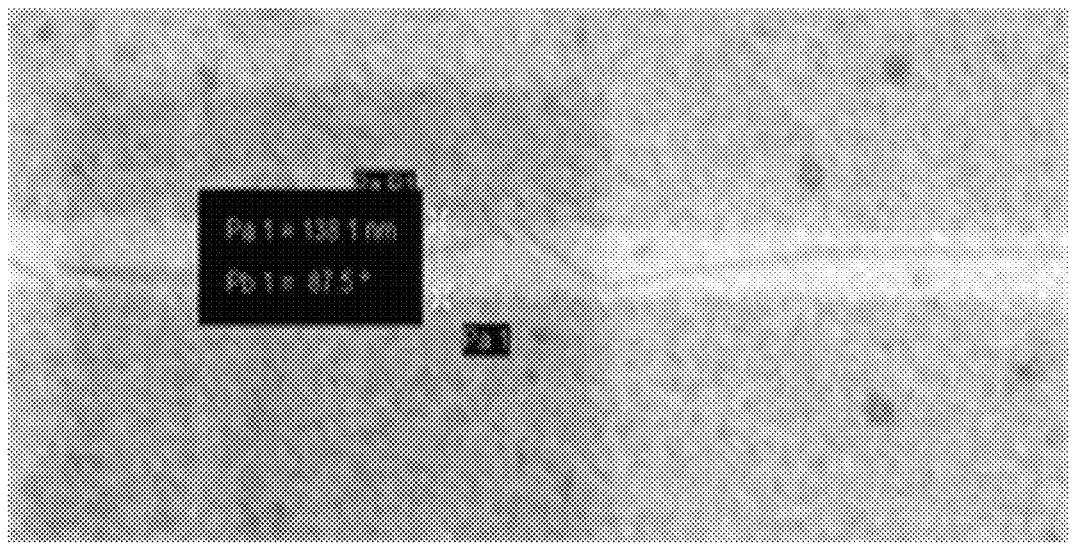
Figure 8A:
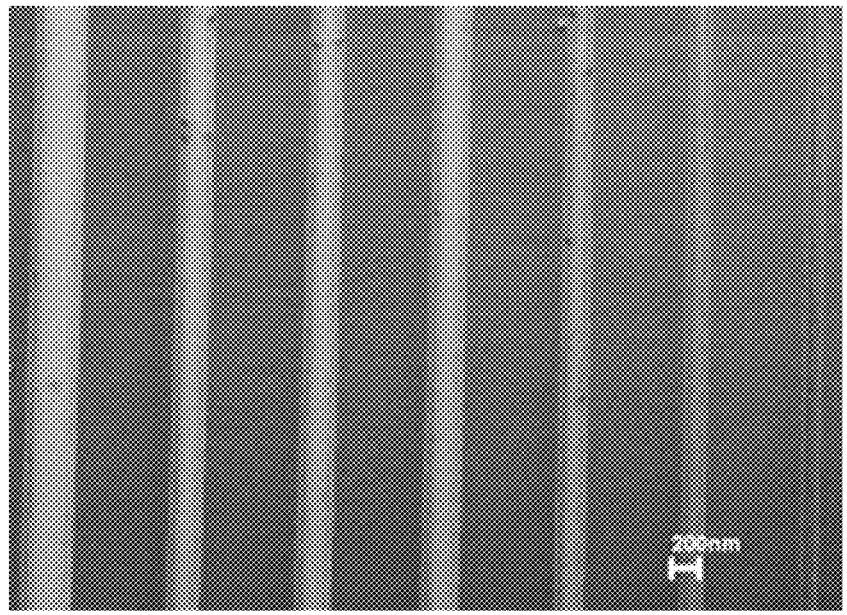
FIG. 8 shows that nanoparticles as small as 15 nm could be assembled in 20 nm trenches without any gaps. The electric field was 1.5 V/cm in FIG. 8A and 2 V/cm in FIG. 8B (scale bars represent 200 nm).
FIG. 8C shows the time dependence of current flow at 1.5, 2, 2.5, and 3 V/cm (traces from bottom to top, respectively).
Figure 8B:
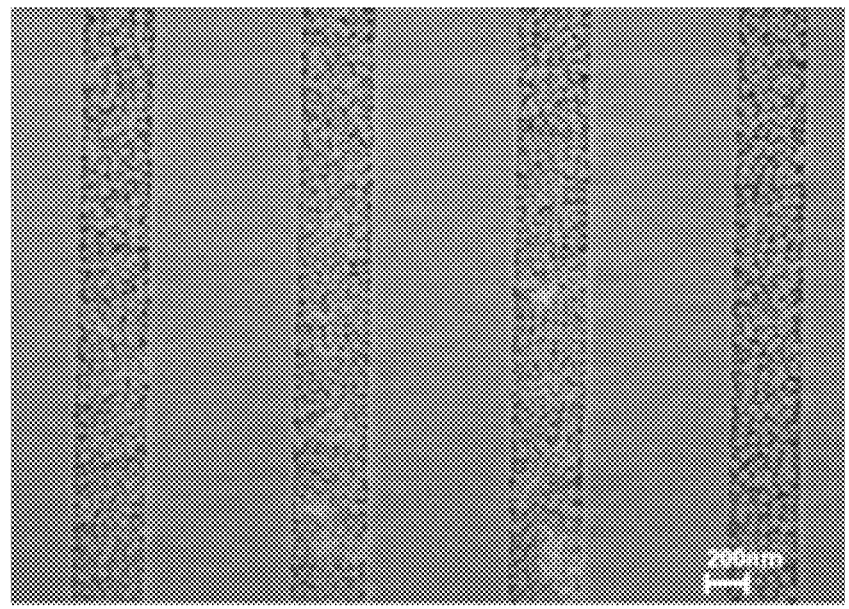
Figure 8C:
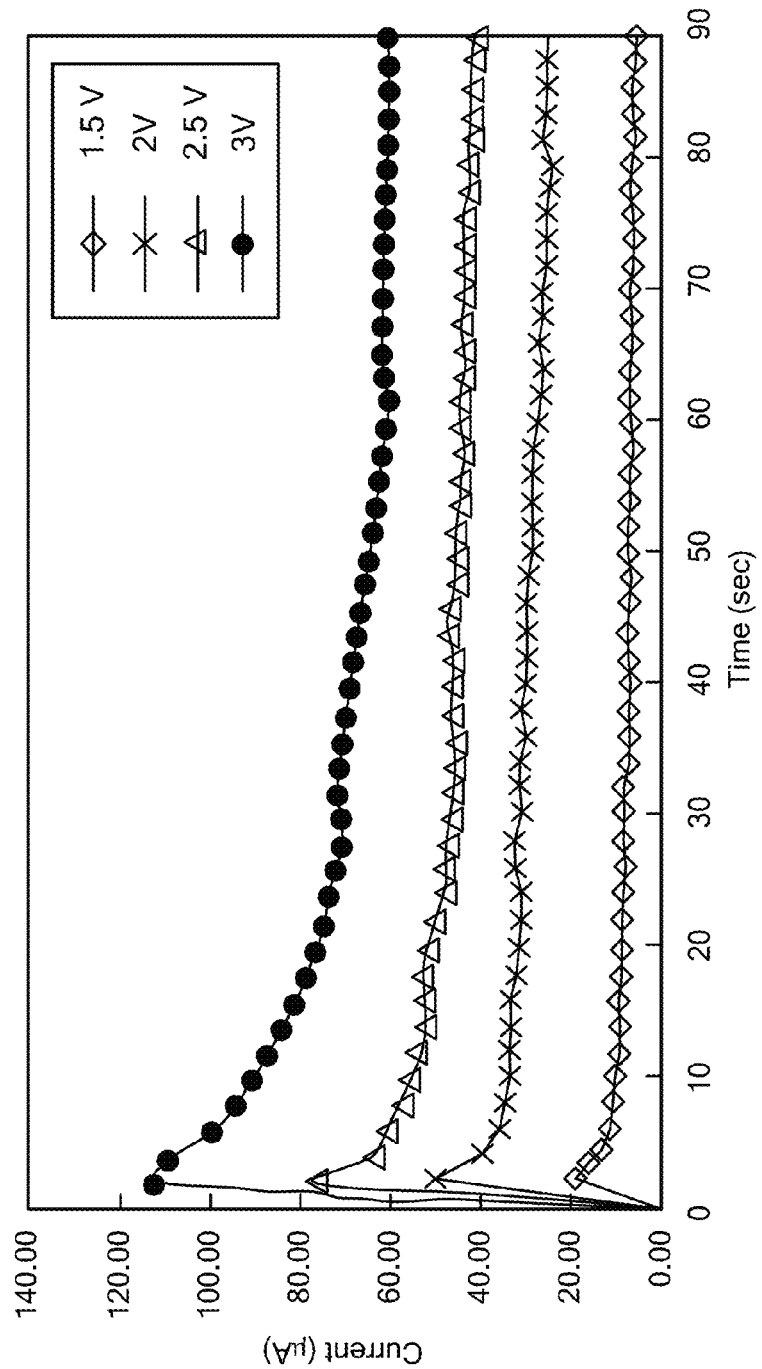
Figure 9:
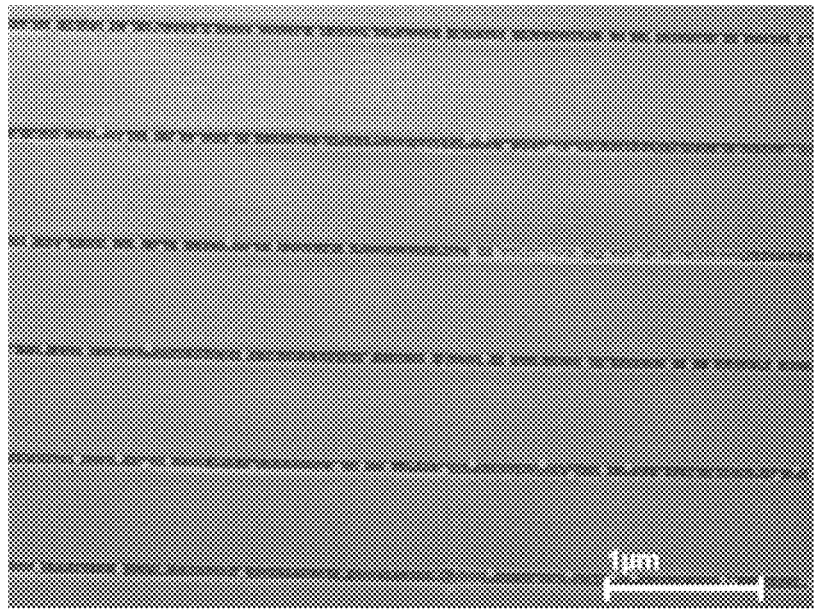
FIG. 9 shows the result of assembling 50 nm polystyrene latex (PSL) nanoparticles in 50 nm wide trenches. A continuous line of particles is visible at the bottom of the trenches, with a few particles visible as a second layer above the first layer.

To investigate the effect of voltage on assembly, the nanosubstrates fabricated for the experiment in Example III were used for assembly driven by an electric field ranging from As seen from the results presented in FIGS. 5 and 7, the density of nanotubes assembled inside a trench of given width was higher when the voltage was increased.

Example V

Assembly of Nanoparticles on Patterned Nanosubstrates

Monodispersed polystyrene latex (PSL) nanoparticles that ranged in diameter from 50 nm-10 nm (obtained from Duke Scientific, Inc.) were diluted in deionized water with a pH value adjusted to 10-11 by adding ammonium hydroxide solution. Colloidal nanoparticles such as PSL and silica particles (also obtained from Duke Scientific, Inc., Palo Alto, Calif.) have negative zeta potentials at high pH values (9-11) in an aqueous solution, and as a result are negatively charged. The electrophoretic assembly experiments were performed by connecting the PMMA patterned gold nanosubstrate (anode) and a bare gold substrate (cathode) to a DC voltage source and dipping them vertically into the particle suspension with a separation between the electrodes of 1 cm. FIGS. 12B and 12C schematically illustrate the assembly of negatively charged colloidal particles onto the PMMA patterned gold substrate.

Figure 10:
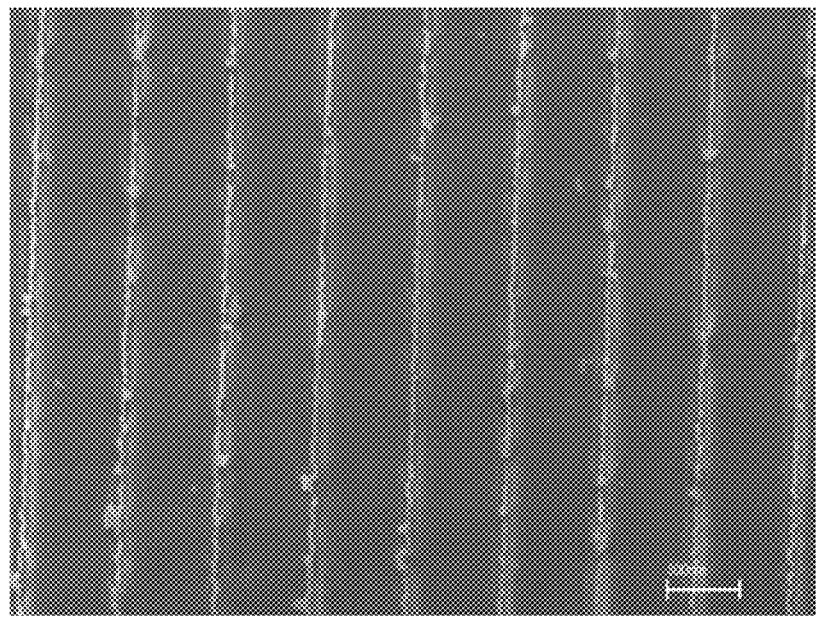
FIG. 10 shows the result of assembling 10-15 nm PSL nanoparticles in 30 nm wide trenches (scale bar represents 100 nm). A continuous line of particles is visible at the bottom of the trenches.
Figure 13A:
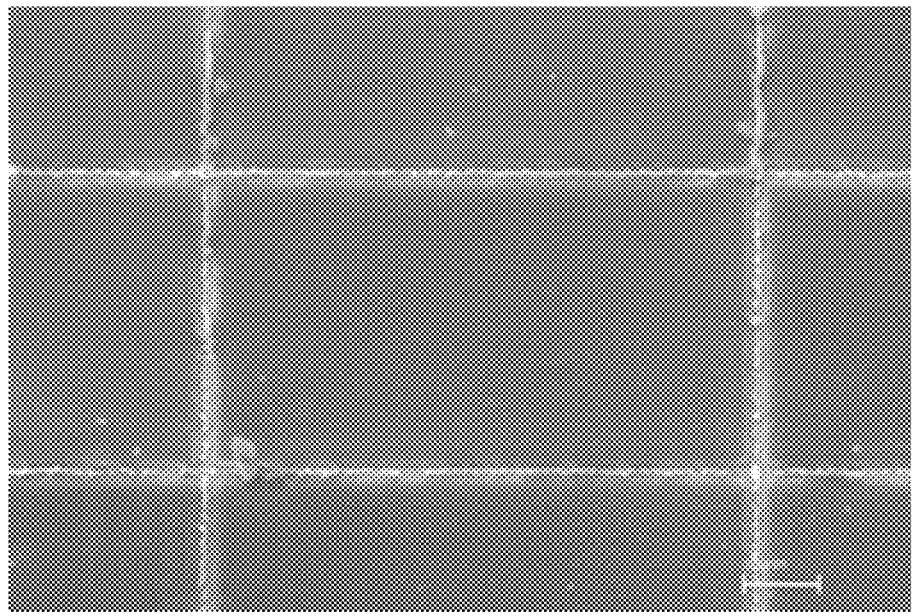
FIG. 13A shows a cross pattern of aligned nanoparticles.
Figure 13B:
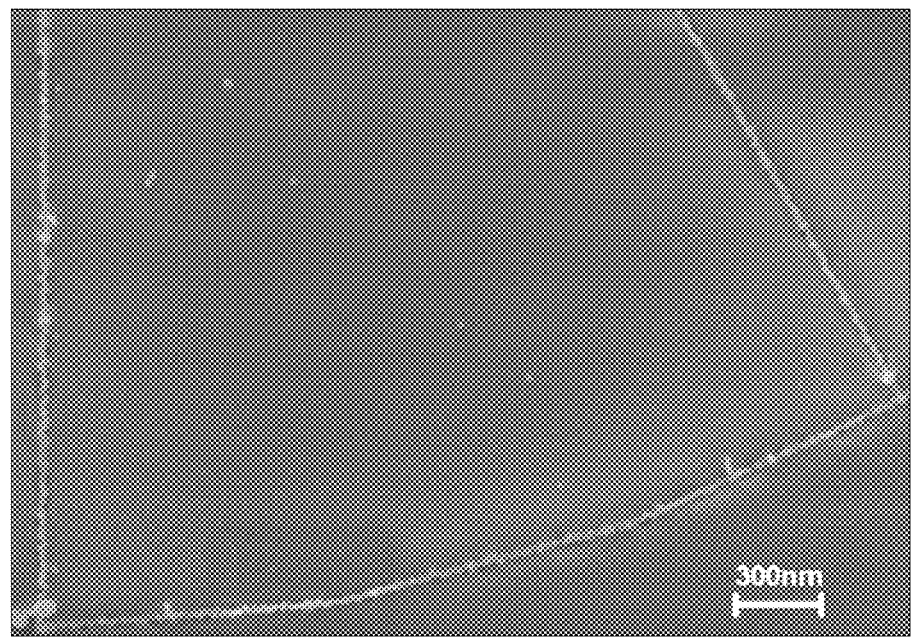
FIG. 13B shows curved and linear aligned nanoparticle assemblies.

FIG. 10 shows that single nanoparticle lines of 10-15 nm wide were assembled in 30 nm wide trenches using 2 V/cm for 90 seconds. The assembled nanoparticles were in continuous, linearly aligned arrangement within the nanotrenches. A more complex cross-line nanoparticle structure also was fabricated using this one-step assembly process (FIG. 13A), proving that the directed assembly is independent of the trench orientation with respect to the template dipping direction. Curved single nanoparticle lines also were assembled (FIG. 13B).

Figure 14A:
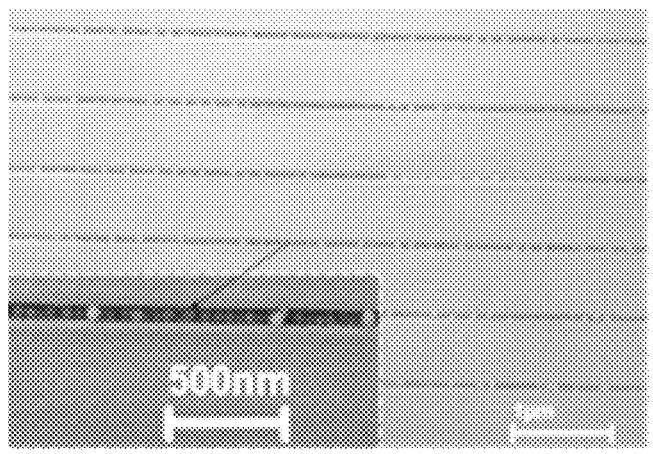
FIG. 14 shows FESEM images of 50 nm PSL particles assembled in (FIG. 14A) 50 nm wide trenches using 2 V/cm for 90 s, (FIG. 14B) trenches with varying widths using 2 V/cm for 90 s, and (FIG. 14C) 260 nm wide trenches using 3V/cm for 90 s.
Figure 14B:
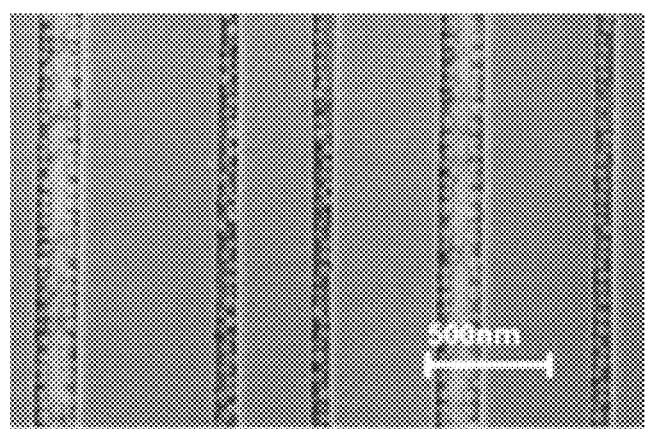
Figure 14C:
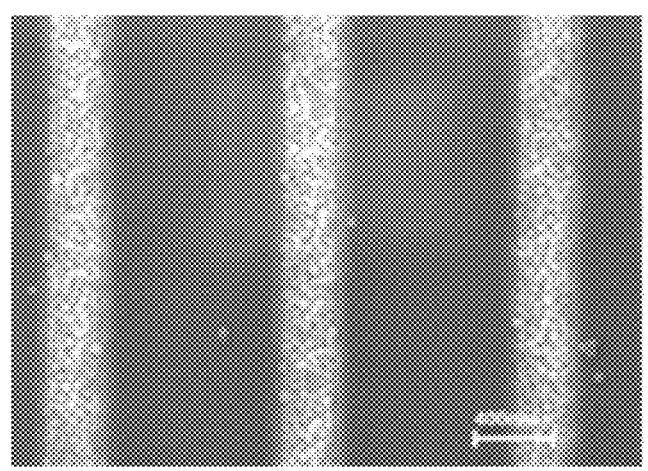

Increasing the nanotrench width to 50 nm allowed the capture of larger size particles into particle lines (FIG. 14A-C), demonstrating that the template assisted electrophoretic assembly method is scalable. Using 2V voltage for 90 s, the 50 nm wide trenches were near fully covered with a first layer of single nanoparticles packed into an array at the trench bottom; a few second layer particles were deposited on top of the first layer of particle lines (see FIG. 14A). This is due to the fact that the assembled particles are insulating and they shield the gold at the bottom of the trench resulting in a much weaker electric field.

Example VI

Biosensor Device Fabrication and Micro-Assembly

A custom Biosensor Microassembly Platform (BMP) was built for assembling a nanoparticles-based microscale in-vivo biosensor. Conducting directed assembly of nanoparticles on a 0.01 $mm^2$ microchip was a challenging problem. Complexities arose from assembling micro-components of different materials, and assembling antibody functionalized nanoparticles into their predetermined nanoscale trenches on the biosensor. Using the designed platform, vision information was merged with motion control, so that precise manipulation of the stages and microscopes facilitated the assembly process of the in-vivo biosensor. Along with Biosensor Microassembly Platform system design and automation, assembly of an in-vivo biosensor was demonstrated having numerous applications in biomedical and health industry.

In building the system, micro/nano scale resolution was considered in manipulating the end effectors for precision assembly. Other challenges in assembly originated from integrating micro-components of different materials, manufactured using different technologies. These challenges required an understanding of the physics of manipulation, and forces involved in the assembly of components in micro/nano domain, which are usually neglected in macro domain (e.g., surface tension, van der Waals, and electrostatic attractions).

Figure 20:
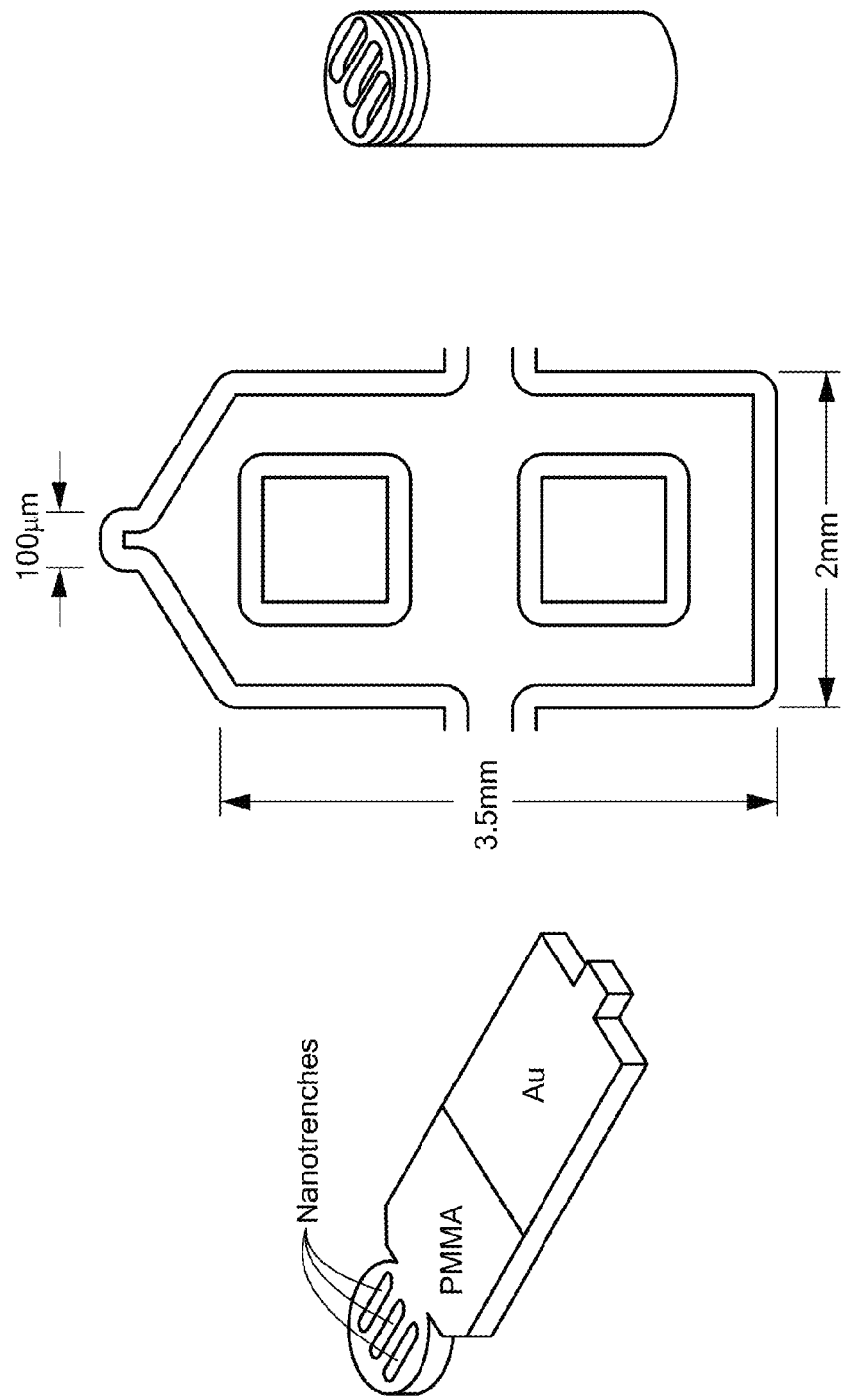
FIG. 20 is a schematic illustration and a representation of a microscopic image of a nanosubstrate, and a schematic illustration of a nanosubstrate on a catheter.

One such device in which nanoparticles were integrated in microsystems was an in-vivo biosensor for detecting multiple biomarkers for several diseases, particularly cancer, with high sensitivity and specificity. The active area in the biosensor consisted of various biomarker coated nanoparticles arranged at regular intervals in nanotrenches generated by E-Beam lithography on a Polymethyl methacrylate (PMMA)/Au/SU8 substrate, as shown in FIG. 20.

Arrangement of the nanoparticles was achieved by a field assisted directed assembly method when applying a voltage through the electrode extension of the active area. Prior to assembly, the bottom part of the active area SU8 substrate was glued to a catheter and after the assembly the catheter with the biosensor active area was broken away from the electrode extension for the biosensor for in-vivo testing. In the in-vivo mode, the biosensor is exposed to a large volume of the blood thereby making very early detection possible.

In the Biosensor Microassembly Platform, computer-based assembly was used to increase efficiency, reliability and to reduce cost. The platform was used for efficient assembly of in-vivo biosensors and drug delivery devices. FIG. 17 shows a schematic of the Biosensor Microassembly Platform.

Assembly of an in-vivo biosensor was conducted according to the following steps: 1. Move Biosensor Microassembly Platform to a home position to initialize the system. 2. Deposit a high viscosity glue onto the top of a smoothly cut 300 micron catheter by bringing the needle into contact with the catheter. 3. Glue the 100 micron biosensor chip to the catheter utilizing biocompatible glue. 4. Assemble the antibody coated nanoparticles into the nanotrenches of the biosensor chip. 5. Break the biosensor chip holder, and store the in-vivo biosensor for testing.

Manipulation System

To manipulate the end effectors (biosensor holder head and catheter holder), a single-axis linear long travel (50 mm) stages were bolted together in XY or XYZ configuration for cases where movement was required in more than one axis, resulting in a multi-degree of freedom (DOF) system. For precise manipulation, linear encoded long travel stages with resolution in 100 nm range were used. These linear encoded stages were incorporated with a linear encoder sensor and a smart signal electronics module. When the stages were driven by a stepper motor actuator, all programmable and diagnostic features were enabled via Advanced Positioning Technology (APT) server software.

Biosensor Holder Head and Catheter Holder Design

Figure 21:
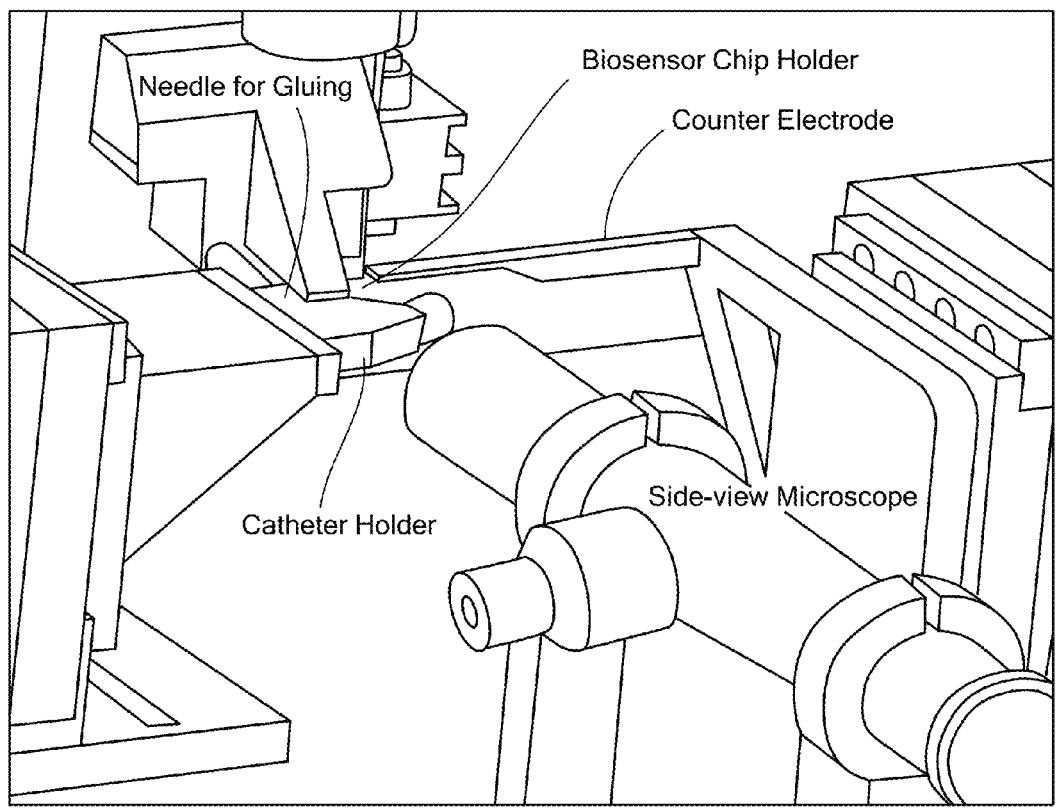
FIG. 21 is a schematic illustration of a manipulation area for a biosensor microassembly platform.

For holding the biosensor chips during assembly, a biosensor holder head was designed (shown in FIG. 21) to hold the base of the biosensor chip while conducting assembly. The Biosensor Holder Head included a needle adapter for attaching a needle used for applying glue onto the tip of the catheter, clamp with spring for holding the biosensor base intact during the particle assembly process, working electrode used as anode for electrophoresis assembly to take place, trench for positioning the wire which provided the electric voltage of the working electrode. For holding the catheter upright during assembly process, a catheter holding clamp was designed.

Counter-Electrode Platform for Particle Assembly

Figure 22:
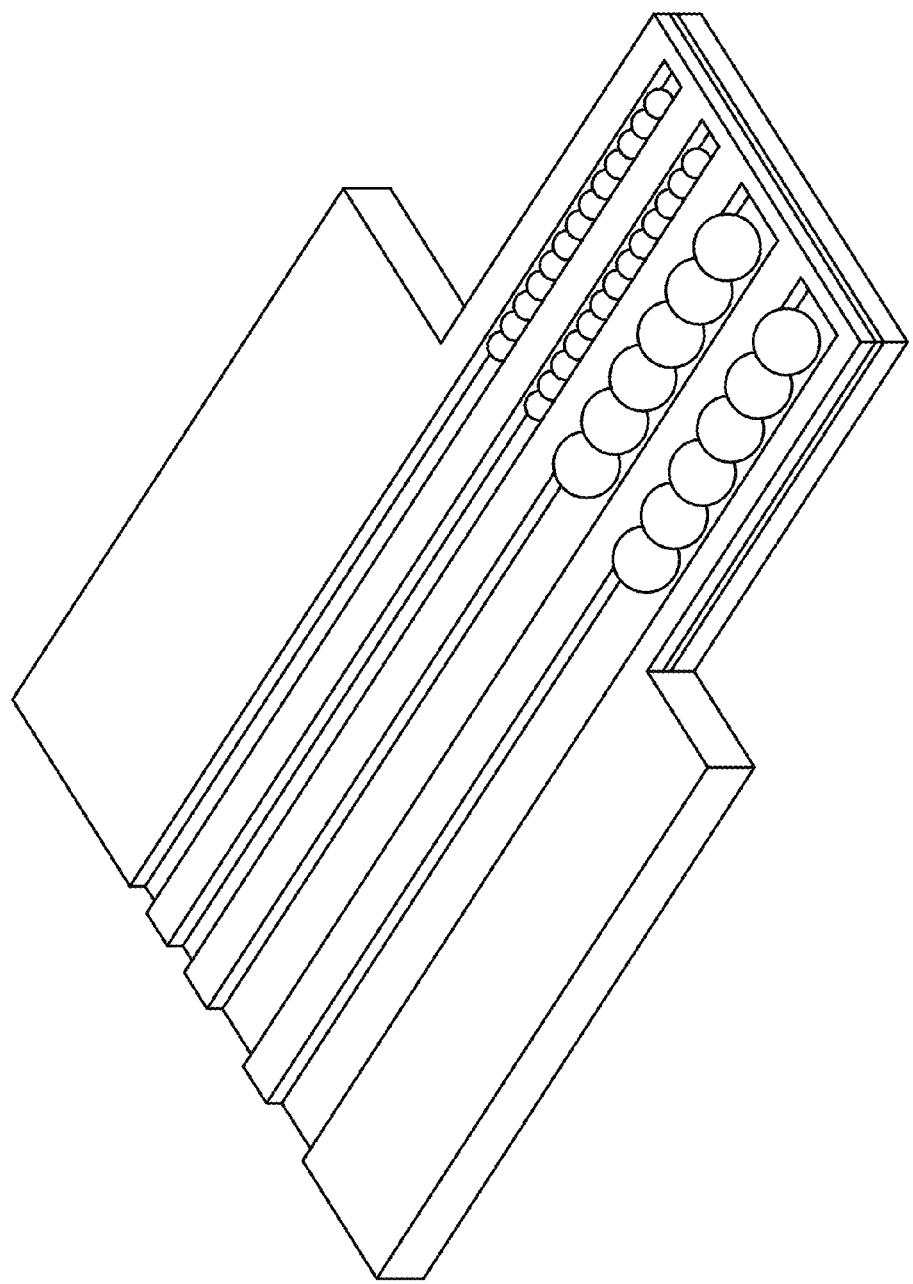
FIG. 22 is a schematic illustration of biomarker coated nanoparticles assembled on trenches of a nanosubstrate.

A counter-electrode was used in performing electrophoretic assembly; whereby non-uniform electric fields were utilized to direct the large scale assembly of the nanoparticles into nanoscale structures over large areas. Using micro and nanoscale templates, various nanoparticles were directly and selectively assembled (by size) into nanotrenches. The assembly process was governed by electric field, time period, and dimension of the trench geometry. With the counter electrode probe as the cathode and the gold coated trenches on the template as the anode, the nanoparticles were directed toward nanotrenches. This approach was used to fabricate unique structures comprised of functionalized nanoparticles over a large area of the template (see FIGS. 22 and 23).

Particle Solution Injection Setup

Figure 23:
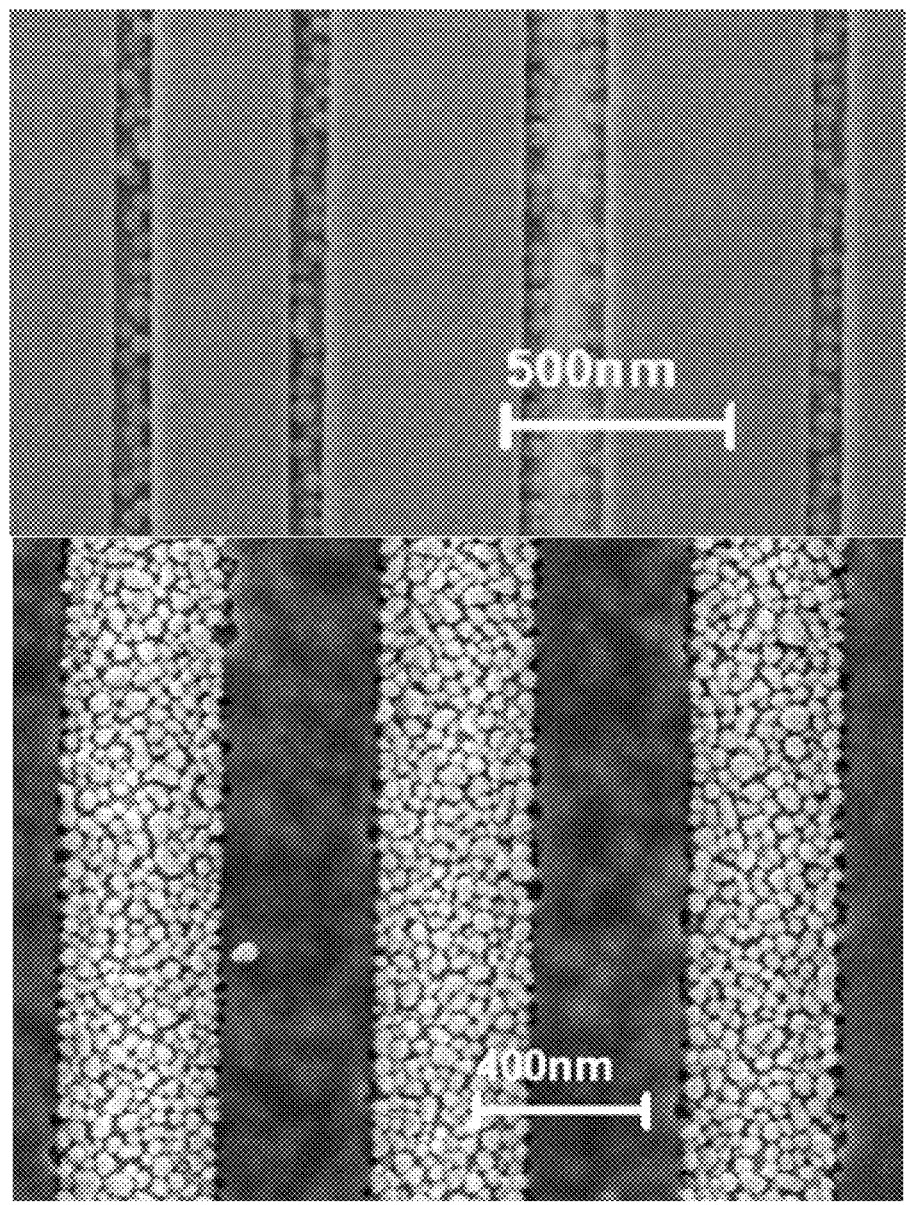
FIG. 23 is a representation of PSL nanoparticles assembled into nanotrenches of a nanosubstrate.

For delivery of particle solution in precise amounts, a software controlled microinjection setup was incorporated with the platform. FIG. 23 shows assembly of nanoparticles into nanotrenches.

Vision System

In this platform, vision of the assembly process was an important feature, since the orientation of the microscopes, working distance (focal length), and magnification of the objectives are important features that needed to be considered in designing the vision system. In the vision system, Charge-Coupled Device (CCD) cameras were attached to objectives for top and side view of the assembly process. The microscope system consisted of CCD camera mounted to an objective along with an infinitube in-line assembly with a co-axial illuminator connected in-line with the optics to provide illumination. These microscope systems for top and side view were held by holders which were attached to XY stage with two degrees of freedom, so that image processing and focusing was directly controlled by the platform software. One of the most significant features of this design was that the stages and microscopes precisely aligned such that the limited degree of freedom of the catheter holder, the biosensor holder head, and the top and side view microscopes did not affect the assembly process.

Motion Control

The motion control of the platform was achieved by using Advanced Positioning Technology modular rack system that allowed the programming of 12 channel platform in parallel. Using a USB communications interface, the APT rack system was incorporated with the platform, resulting in precision control of all linear stages connected to the channels. In these experiments, the diameter of catheter was 300 μm (smaller catheters could also be used), and the fabricated biosensor chip size ranged between 100 μm and 250 μm. Therefore, the aim of motion control was to implement automated assembly tasks with a precision of few microns.

Vision Control

A dual camera system was used for image acquisition. To achieve direct control of this vision system, the cameras were connected to the central computer for online tracking of assembly process and image processing operations coded in vision control software.

Particle Injection System Control

Figure 24:
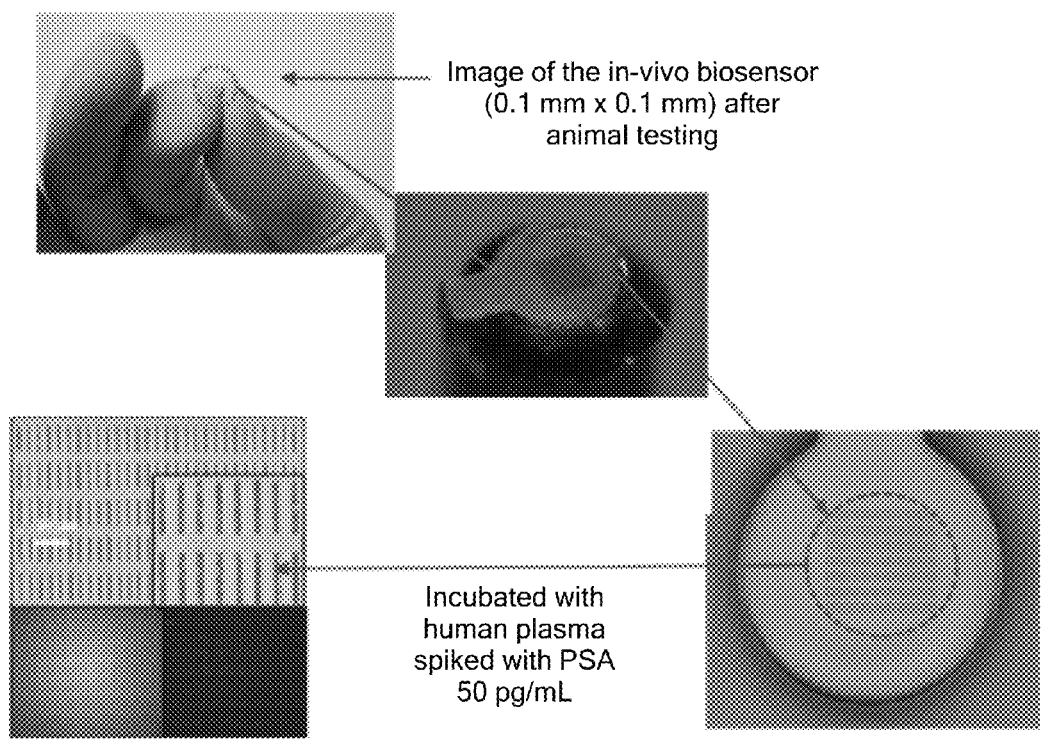
FIG. 24 are representations of images of an in-vivo biosensor for animal testing.

A Harvard Apparatus PHD 2000 series pump was used, which employs a microcontroller that controls a small step angle stepping motor that drives the syringes containing particle solution. The control commands from the software platform were interfaced via an RS-232 to allow different infusion and refill rate of the syringes in delivering particle solution for nanoparticles assembly on the biochip. FIG. 24 shows the size and a close-up of an in-vivo biosensor.

Example VII

Assembly of Antibody-Coated Nanoparticles

Figure 18:
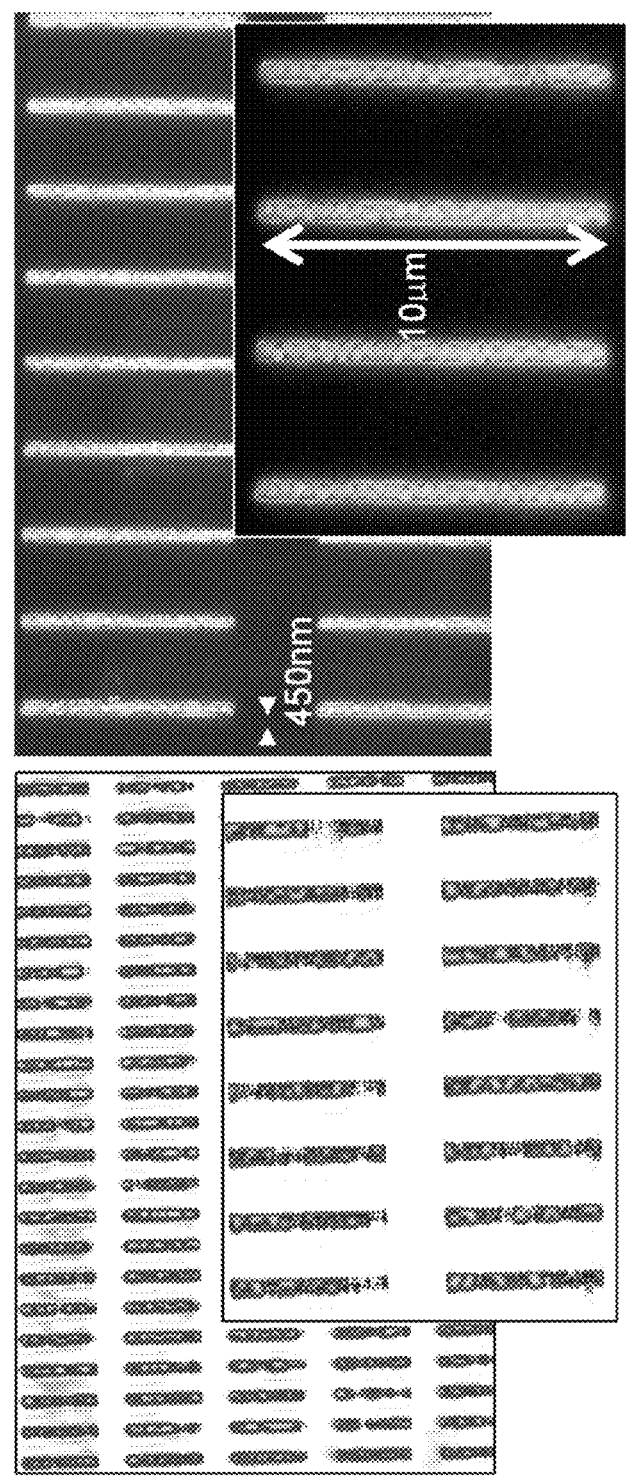
FIG. 18 is a representation of an SEM micrograph of 350 nm IgG-coated carboxylic functionalized PSL (left) and 350 nm 2C5-coated carboxylic functionalized PSL particles assembled into 400 nm wide and 10 micron long nanotrenches with 3 micron spacing.

Prostate Specific Antigen (PSA), IgG antibody, monoclonal antibody 2C5 (mAb 2C5), and mouse anti-CEA coated carboxyl 320 nm polystyrene particles were prepared. FIG. 18 shows an SEM micrograph of 350 nm IgG-coated carboxylic functionalized PSL particles (left) and 350 nm 2C5-coated carboxylic functionalized PSL particles assembled into 400 nm wide and 10 micron long trenches with 3 micron spacing.

Figure 19:
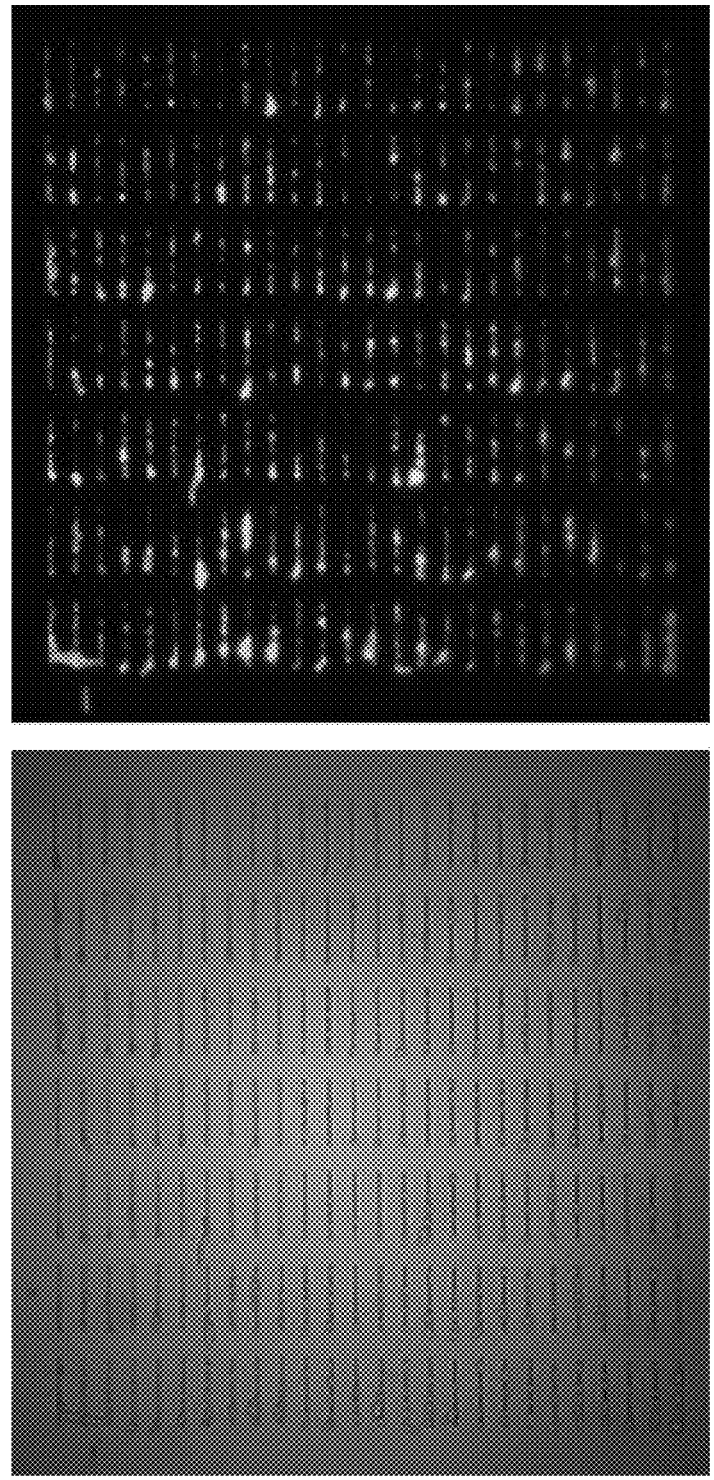
FIG. 19 is a representation of bright field (left) and fluorescent images of 350 nm fluorescent tagged 2C5-coated carboxylic functionalized PSL particles assembled into 500 nm wide trenches with 3 micron spacing.

As shown in FIG. 19, assembly experiments with fluorescent tagged 2C5-coated carboxylic functionalized nanoparticles demonstrated that the antibody remained absorbed on the surface of nanoparticles during the assembly process.

Example VIII

Use of 2C5 Coated PSL Particles Assembled Microchips to Detect Nucleohistone Antigen Following the preparation of 2C5 coated PSL particles (as described in Example VII), they were assembled in the trenches of the biosensor chip and tested for detection of Nucleohistone (NHS) antigen. NHS antigen was labeled with a fluorophore such as FITC, which can enable detection on the microchips. The chips were blocked overnight with 2% Bovine Serum Albumin in D.I water. Labeled NHS in HBS pH 7.4 was incubated with 2C5 microchips at varying concentration (at 4° C.), with IgG microchips as IgG is a generic antibody that shows no specificity towards any antigen and was used as a control.

2C5 microchips were able to detect as low as 125 pg/ml of labeled antigen compared to IgG microchips, which did not show any specificity towards labeled antigen. This shows the specificity of mouse mAb 2C5 towards nucleosomes.

Similarly, the effect of concentration on the detection of various concentrations of labeled nucleosome in blood was investigated. About 1-2 ml of blood was obtained from Balb/c female mice. The blood was spiked with various concentration of labeled NHS antigen. The experiment was performed in a manner similar to the above experiment except that the 2C5 microchips were incubated with blood samples spiked with labeled NHS antigen for a period of one hour, then washed and imaged using bright field and fluorescent microscopy.

2C5 microchips were able to detect labeled nucleosome. The 2C5 chips detected labeled nucleosome in a dose response manner from 200 µg/ml to 50 µg/ml.

Example IX

Use of Anti-CEA PSL Particles Assembled Microchips

Figure 25:
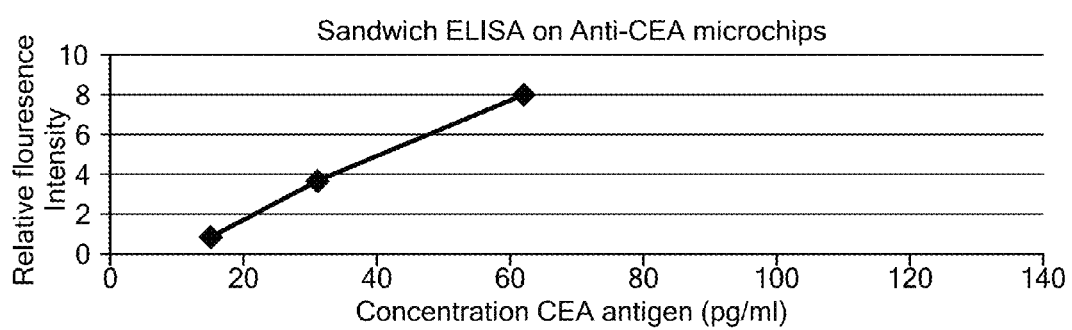
FIG. 25 is a graphic representation of a sandwich ELISA performed on anti-CEA microchips.

Anti-CEA microchips were assembled as described in Example VII. Following the assembly, the chips were blocked overnight with 2% Bovine Serum Albumin in D.I. water. The Anti-CEA PSL Particles were able to detect 15 pg/ml of CEA antigen and was detected by sandwich ELISA, where the detection antibody was labeled with FITC. A dose response curve was observed with varying amounts of CEA incubated with the microchips, as shown in FIG. 25.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A nanosubstrate comprising:
a substrate layer comprising a photoresist material;
a conductive layer deposited on the substrate layer;
an insulating layer deposited on the conductive layer, the insulating layer interrupted by two or more nanotrenches or nanowells having different widths, the widths being at least about 20 nm; and
one or more nanoparticles deposited in each of the two or more nanotrenches or nanowells, the nanoparticles belonging to two or more different size classes, wherein the nanoparticles in each size class have a diameter less than or equal to the width of the nanotrench or nanowell in which they are deposited, and wherein the nanoparticles of each size class are covalently bound to a different antibody or antigen binding fragment thereof.

2. The nanosubstrate of claim 1, wherein the nanosubstrate comprises an area of about 0.01 mm² to about 0.1 mm².

3. The nanosubstrate of claim 1, wherein the conductive layer comprises an organic or inorganic conductor.

4. The nanosubstrate of claim 3, wherein the conductive layer comprises gold, aluminum, copper, polyanaline, or a combination thereof.

5. The nanosubstrate of claim 1, wherein the insulating layer comprises a photoresist material.

6. The nanosubstrate of claim 5, wherein the photoresist material is SU-8.

7. The nanosubstrate of claim 1, wherein the thickness of the conductive layer is about 40 nm to about 100 nm.

8. The nanosubstrate of claim 1, wherein the thickness of the insulating layer is about 80 nm to about 150 nm.

9. A catheter comprising the nanosubstrate of claim 1.

10. The nanosubstrate of claim 1, wherein the deposited nanoparticles are electrophoretically deposited.

11. The nanosubstrate of claim 1, further comprising an adhesion layer beneath said substrate and an additional substrate beneath said adhesion layer.

12. The nanosubstrate of claim 11, wherein said additional substrate comprises silicon.

13. The nanosubstrate of claim 1, wherein the nanosubstrate comprises a biosensor active area containing said nanotrenches or nanowells and an electrode extension devoid of nanotrenches or nanowells.

14. The nanosubstrate of claim 13, wherein the electrode extension comprises a plurality of nanowires, each nanowire formed from an extension of the conductive layer at the base of a single nanotrench or nanowell.

15. The nanosubstrate of claim 13, wherein the biosensor active area is suitable for being broken off from the electrode extension.

16. The nanosubstrate of -further comprising an antigen bound to said antibody or antigen binding fragment.

17. The nanosubstrate of claim 16 further comprising a detection antibody bound to said antigen.

18. The nanosubstrate of claim 17, wherein the detection antibody is fluorescently labeled.

19. The nanosubstrate of claim 18 comprising a plurality of bound antigens and a plurality of bound detection antibodies.

20. The nanosubstrate of claim 19, wherein the position of fluorescence on said nanosubstrate indicates the type of antigen bound to the nanosubstrate.

21. The nanosubstrate of claim 1 that can detect 100 biomarkers.

22. The nanosubstrate of claim 21 that can detect 1000 biomarkers.

23. The nanosubstrate of claim 1 that can detect a biomarker diagnostic for a hyperproliferative, hyperplastic, metaplastic, dysplastic, or pre-neoplastic disease or disorder or for a cancerous condition.

24. The catheter of claim 9 that is inserted into the body of a subject.

25. The catheter of claim 9 that is contacted with a biological sample of a subject.

26. The nanosubstrate of claim 1 having a plurality of said nanotrenches or nanowells arranged in an array.

27. The nanosubstrate of claim 1, wherein the insulating layer comprises poly(methyl methacrylate).

* * * * *